United States Patent
Kitano et al.

Patent Number: 5,183,587
Date of Patent: Feb. 2, 1993

[54] LIQUID CRYSTALLINE COMPOUND

[75] Inventors: Kisei Kitano; Makoto Ushioda, both of Chibashi; Manabu Uchida; Toshiharu Suzuki, both of Ichiharashi, all of Japan

[73] Assignee: Chisso Corporation, Osaka, Japan

[21] Appl. No.: 454,988

[22] Filed: Dec. 22, 1989

[30] Foreign Application Priority Data

Jan. 6, 1989 [JP] Japan .................................. 64-1004

[51] Int. Cl.$^5$ .................. C09K 19/30; C09K 19/52; C07C 43/225; C07C 28/00; C07C 25/00
[52] U.S. Cl. .................. 252/299.63; 252/299.01; 568/585; 568/588; 568/669; 570/127; 570/131
[58] Field of Search .................. 252/299.01, 299.63; 568/585, 588, 669; 570/127, 131, 186

[56] References Cited

U.S. PATENT DOCUMENTS

| | | | |
|---|---|---|---|
| 4,877,548 | 10/1989 | Kitano et al. | 252/299.63 |
| 4,880,562 | 11/1989 | Kitano et al. | 252/299.63 |

FOREIGN PATENT DOCUMENTS

| | | |
|---|---|---|
| 0325796 | 8/1989 | European Pat. Off. |
| 0330216 | 8/1989 | European Pat. Off. |
| WO88/08441 | 11/1988 | PCT Int'l Appl. |

OTHER PUBLICATIONS

Chemistry Letters: vol. 2, Feb. 1989, pp. 309–312, The Chemol. Society of Japan, Uno et al.: "A Novel Generation and Behavior of Alkylfluorocarbenoids from α,α-Chlorofluoroalkyl Sulfoxides".

*Primary Examiner*—Robert L. Stoll
*Assistant Examiner*—Shean C. Wu
*Attorney, Agent, or Firm*—Wenderoth, Lind & Ponack

[57] ABSTRACT

A liquid crystal compound having a relatively low viscosity, a superior compatibility with other liquid crystalline compounds and suitable for preparing a liquid crystal device having a high response rate, and a superior liquid crystal composition containing the compound are provided, which compound is expressed by the formula

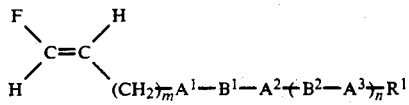

wherein $R^1$ is H, F, Cl, CN or 1-20C alkyl or alkenyl in which alkenyl one —$CH_2$— group or two not adjacent —$CH_2$— groups may be replaced by —O— and in which alkenyl the position and number of the double bond may be optionally chosen; $A^1$, $A^2$ and $A^3$ are

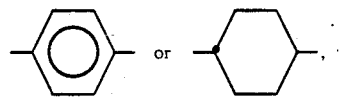

the H atom(s) of which

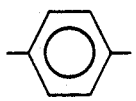

may be replaced by F, Cl or methyl; $B^1$ and $B^2$ are —$CH_2CH_2$—, —$CH_2O$—, —$OCH_2$— or single bond; n is 0 or 1; and m is 0 to 20.

9 Claims, No Drawings

LIQUID CRYSTALLINE COMPOUND

BACKGROUND OF THE INVENTION

This invention relates to a novel liquid crystalline compound and a liquid crystal composition containing the compound.

Liquid crystal substances and compositions containing the same have been used for various display devices, utilizing the dielectric anisotropy (abbreviated to $\Delta\epsilon$) and optical anisotropy (abbreviated to $\Delta n$) in the liquid crystal phases thereof.

Liquid crystal display modes include various modes such as electrically controlled birefringence mode (ECB mode), twisted nematic mode (TN mode), super-twisted birefringence mode (SBE mode), dynamic scattering mode (DS mode), guest-host mode, etc., correspondingly to the electrooptical effect applied.

Liquid crystal materials used for display devices should be together provided with various characteristics such as broad mesomorphic range, low viscosity, large positive $\Delta\epsilon$ value or negative $\Delta\epsilon$ value, less temperature dependence of electrooptic characteristics (especially threshold voltage) of display devices within a wide temperature range, etc., depending on the display mode of the devices and further depending on various characteristics required for display elements.

At present, however, there is no single compound which is practically usable in the aspects of mesomorphic range, driving voltage and response properties. Thus, a mixture of several kinds of liquid crystal compounds or a mixture of several kinds of liquid crystal compounds with a compound having latent liquid crystal properties or a non-liquid crystal compound has been practically used.

SUMMARY OF THE INVENTION

The object of the present invention is to provide a liquid crystalline compound and a liquid crystal composition usable for liquid crystal display devices. The liquid crystalline compound referred to herein means not only compounds exhibiting liquid crystal phases but also compounds which usually exhibit no liquid crystal phase, but when dissolved in other liquid crystal compounds, effectively function in a certain aspect of liquid crystal behavior.

The present invention in a first aspect resides in a compound expressed by the formula

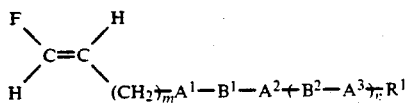

(I)

wherein $R^1$ represents a hydrogen atom, a fluorine atom, a chlorine atom, a cyano group, or an alkyl group or an alkenyl group each of 1 to 20 carbon atoms in which one —CH$_2$— group or two non-adjacent —CH$_2$— groups may be replaced by —O— group, and in which alkenyl group the position and number of the double bond may be optionally chosen; $A^1$, $A^2$ and $A^3$ each independently represent

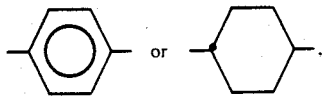

the hydrogen atom(s) of which

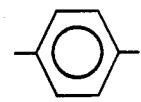

may be replaced by fluorine atom(s), chlorine atom(s) or methyl group(s); $B^1$ and $B^2$ each independently represent —CH$_2$CH$_2$—, —CH$_2$O—, —OCH$_2$— or a single bond; n represents an integer of 0 or 1; and m represents an integer of 0 to 20.

The present invention in a second aspect resides in a liquid crystal composition containing at least one member of the compound expressed by the above formula (I).

DETAILED DESCRIPTION OF PREFERRED EMBODIMENTS

Preferred examples of the compound of the formula (I) of the present invention wherein n=0 are compounds represented by the following formulas:

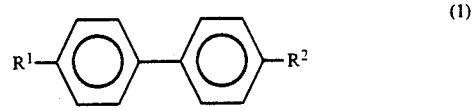
(1)

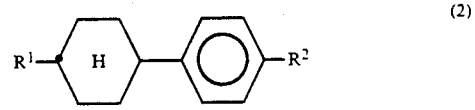
(2)

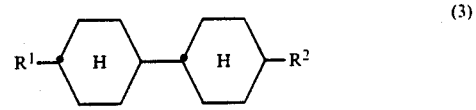
(3)

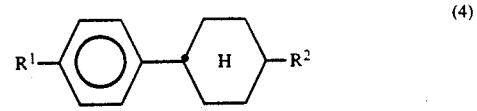
(4)

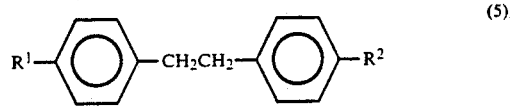
(5)

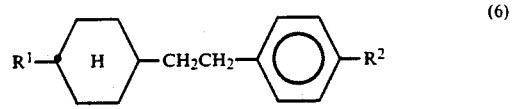
(6)

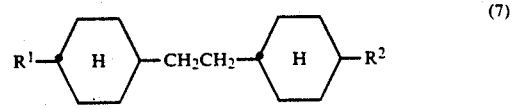
(7)

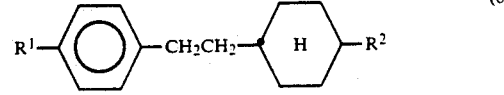
(8)

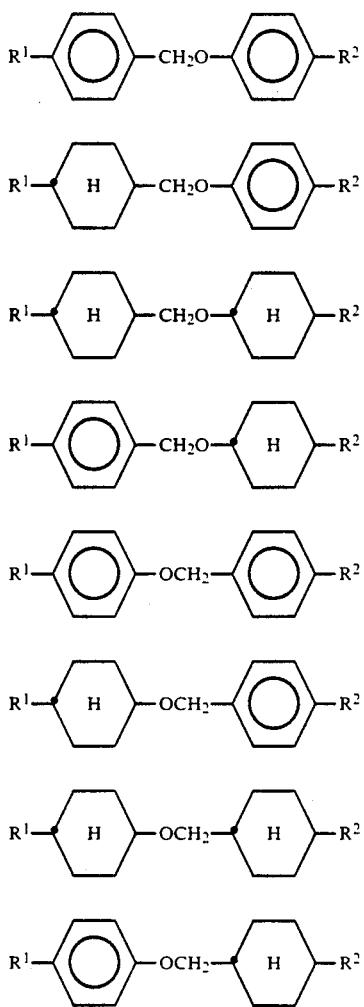

In these formulas, R$^1$ is as defined above, R$^2$ represents

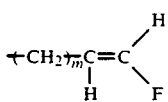

wherein m represents an integer of 0 to 20, and the phenylene ring may be replaced by

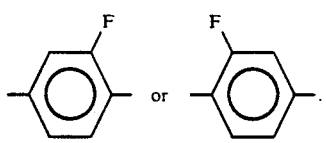

Among the compounds of the formulas (1) to (16), those wherein m in R$^2$ is an integer of 0 to 6 are preferred. Among the compounds of the formulas (1) to (16), those of the formulas (1) to (8) are particularly preferred. Representative examples of further particularly preferable compounds are as follows:

Trans-1-(E-2-fluoro-1-ethenyl)-4-(4-cyanophenyl)cyclohexane
Trans-1-(E-3-fluoro-2-propenyl)-4-(4-cyanophenyl)cyclohexane
Trans-1-(E-4-fluoro-3-butenyl)-4-(4-cyanophenyl)cyclohexane
Trans-1-(E-5-fluoro-4-pentenyl)-4-(4-cyanophenyl)cyclohexane
Trans-1-(E-6-fluoro-5-hexenyl)-4-(4-cyanophenyl)cyclohexane
Trans-1-(E-7-fluoro-6-heptenyl)-4-(4-cyanophenyl)cyclohexane
Trans-1-(E-8-fluoro-7-octenyl)-4-(4-cyanophenyl)cyclohexane
Trans-1-(E-2-fluoro-1-ethenyl)-4-(4-fluorophenyl)cyclohexane
Trans-1-(E-3-fluoro-2-propenyl)-4-(4-fluorophenyl)cyclohexane
Trans-1-(E-4-fluoro-3-butenyl)-4-(4-fluorophenyl)cyclohexane
Trans-1-(E-5-fluoro-4-pentenyl)-4-(4-fluorophenyl)cyclohexane
Trans-1-(E-6-fluoro-5-hexenyl)-4-(4-fluorophenyl)cyclohexane
Trans-1-(E-7-fluoro-6-heptenyl)-4-(4-fluorophenyl)cyclohexane
Trans-1-(E-8-fluoro-7-octenyl)-4-(4-fluorophenyl)cyclohexane
Trans-1-(E-2-fluoro-1-ethenyl)-4-(3-fluoro-4-cyanophenyl)cyclohexane
Trans-1-(E-3-fluoro-2-propenyl)-4-(3-fluoro-4-cyanophenyl)cyclohexane
Trans-1-(E-4-fluoro-3-butenyl)-4-(3-fluoro-4-cyanophenyl)cyclohexane
Trans-1-(E-5-fluoro-4-pentenyl)-4-(3-fluoro-4-cyanophenyl)cyclohexane
Trans-1-(E-6-fluoro-5-hexenyl)-4-(3-fluoro-4-cyanophenyl)cyclohexane
Trans-1-(E-7-fluoro-6-heptenyl)-4-(3-fluoro-4-cyanophenyl)cyclohexane
Trans-1-(E-8-fluoro-7-octenyl)-4-(3-fluoro-4-cyanophenyl)cyclohexane
Trans-1-(E-2-fluoro-1-ethenyl)-4-(3,4-difluorophenyl)cyclohexane
Trans-1-(E-3-fluoro-2-propenyl)-4-(3,4-difluorophenyl)cyclohexane
Trans-1-(E-4-fluoro-3-butenyl)-4-(3,4-difluorophenyl)cyclohexane
Trans-1(E-5-fluoro-4-pentenyl)-4-(3,4-difluorophenyl)cyclohexane
Trans-1-(E-6-fluoro-5-hexenyl)-4-(3,4-difluorophenyl)cyclohexane
Trans-1-(E-7-fluoro-6-heptenyl)-4-(3,4-difluorophenyl)cyclohexane
Trans-1-(E-8-fluoro-7-octenyl)-4-(3,4-difluorophenyl)cyclohexane
Trans-1-(E-2-fluoro-1-ethenyl)-4-(trans-4-cyanocyclohexyl)cyclohexane
Trans-1-(E-3-fluoro-2-propenyl)-4-(trans-4-cyanocyclohexyl)cyclohexane
Trans-1-(E-4-fluoro-3-butenyl)-4-(trans-4-cyanocyclohexyl)cyclohexane
Trans-1-(E-5-fluoro-4-pentenyl)-4-(trans-4-cyanocyclohexyl)cyclohexane
Trans-1-(E-6-fluoro-5-hexenyl)-4-(trans-4-cyanocyclohexyl)cyclohexane
Trans-1-(E-7-fluoro-6-heptenyl)-4-(trans-4-cyanocyclohexyl)cyclohexane
Trans-1-(E-8-fluoro-7-octenyl)-4-(trans-4-cyanocyclohexyl)cyclohexane 4-(E-2-fluoro-1-ethenyl)-4'-cyanobiphenyl
4-(E-3-fluoro-2-propenyl)-4'-cyanobiphenyl
4-(E-4-fluoro-3-butenyl)-4'-cyanobiphenyl
4-(E-5-fluoro-4-pentenyl)-4'-cyanobiphenyl
4-(E-6-fluoro-5-hexenyl)-4'-cyanobiphenyl
4-(E-7-fluoro-6-heptenyl)-4'-cyanobiphenyl
4-(E-8-fluoro-7-octenyl)-4'-cyanobiphenyl
4-(E-2-fluoro-1-ethenyl)-4'-fluorobiphenyl
4-(E-3-fluoro-2-propenyl)-4'-fluorobiphenyl
4-(E-4-fluoro-3-butenyl)-4'-fluorobiphenyl
4-(E-5-fluoro-4-pentenyl)-4'-fluorobiphenyl
4-(E-6-fluoro-5-hexenyl)-4'-fluorobiphenyl
4-(E-7-fluoro-6-heptenyl)-4'-fluorobiphenyl
4-(E-8-fluoro-7-octenyl)-4'-fluorobiphenyl
4-(E-2-fluoro-1-ethenyl)-3',4'-difluorobiphenyl
4-(E-3-fluoro-2-propenyl)-3',4'-difluorobiphenyl
4-(E-4-fluoro-3-butenyl)-3',4'-difluorobiphenyl
4-(E-5-fluoro-4-pentenyl)-3',4'-difluorobiphenyl
4-(E-6-fluoro-5-hexenyl)-3',4'-difluorobiphenyl
4-(E-7-fluoro-6-heptenyl)-3',4'-difluorobiphenyl
4-(E-8-fluoro-7-octenyl)-3',4'-difluorobiphenyl
4-(E-2-fluoro-1-ethenyl)-3'-fluoro-4'-cyanobiphenyl
4-(E-3-fluoro-2-propenyl)-3'-fluoro-4'-cyanobiphenyl
4-(E-4-fluoro-3-butenyl)-3'-fluoro-4'-cyanobiphenyl
4-(E-5-fluoro-4-pentenyl)-3'-fluoro-4'-cyanobiphenyl
4-(E-6-fluoro-5-hexenyl)-3'-fluoro-4'-cyanobiphenyl
4-(E-7-fluoro-6-heptenyl)-3'-fluoro-4'-cyanobiphenyl
4-(E-8-fluoro-7-octenyl)-3'-fluoro-4'-cyanobiphenyl
1-[Trans-4-(E-2-fluoro-1-ethenyl)cyclohexyl]-2-(4-cyanophenyl)ethane
1-[Trans-4-(E-3-fluoro-2-propenyl)cyclohexyl]-2-(4-cyanophenyl)ethane
1-[Trans-4-(E-4-fluoro-3-butenyl)cyclohexyl]-2-(4-cyanophenyl)ethane
1-[Trans-4-(E-5-fluoro-4-pentenyl)cyclohexyl]-2-(4-cyanophenyl)ethane
1-[Trans-4-(E-6-fluoro-5-hexenyl)cyclohexyl]-2-(4-cyanophenyl)ethane
1-[Trans-4-(E-7-fluoro-6-heptenyl)cyclohexyl]-2-(4-cyanophenyl)ethane
1-[Trans-4-(E-8-fluoro-7-octenyl)cyclohexyl]-2-(4-cyanophenyl)ethane
1-[Trans-4-(E-2-fluoro-1-ethenyl)cyclohexyl]-2-(4-fluorophenyl)ethane
1-[Trans-4-(E-3-fluoro-2-propenyl)cyclohexyl]-2-(4-fluorophenyl)ethane
1-[Trans-4-(E-4-fluoro-3-butenyl)cyclohexyl]-2-(4-fluorophenyl)ethane
1-[Trans-4-(E-5-fluoro-4-pentenyl)cyclohexyl]-2-(4-fluorophenyl)ethane
1-[Trans-4-(E-6-fluoro-5-hexenyl)cyclohexyl]-2-(4-fluorophenyl)ethane
1-[Trans-4-(E-7-fluoro-6-heptenyl)cyclohexyl]-2-(4-fluorophenyl)ethane
1-[Trans-4-(E-8-fluoro-7-octenyl)cyclohexyl]-2-(4-fluorophenyl)ethane
1-[Trans-4-(E-2-fluoro-1-ethenyl)cyclohexyl]-2-(3,4-difluorophenyl)ethane
1-[Trans-4-(E-3-fluoro-2-propenyl)cyclohexyl]-2-(3,4-difluorophenyl)ethane
1-[Trans-4-(E-4-fluoro-3-butenyl)cyclohexyl]-2-(3,4-difluorophenyl)ethane
1-[Trans-4-(E-5-fluoro-4-pentenyl)cyclohexyl]-2-(3,4-difluorophenyl)ethane
1-[Trans-4-(E-6-fluoro-5-hexenyl)cyclohexyl]-2-(3,4-difluorophenyl)ethane
1-[Trans-4-(E-7-fluoro-6-heptenyl)cyclohexyl]-2-(3,4-difluorophenyl)ethane
1-[Trans-4-(E-8-fluoro-7-octenyl)cyclohexyl]-2-(3,4-difluorophenyl)ethane
1-[Trans-4-(E-2-fluoro-1-ethenyl)cyclohexyl]-2-(3-fluoro-4-cyanophenyl)ethane
1-[Trans-4-(E-3-fluoro-2-propenyl)cyclohexyl]-2-(3-fluoro-4-cyanophenyl)ethane
1-[Trans-4-(E-4-fluoro-3-butenyl)cyclohexyl]-2-(3-fluoro-4-cyanophenyl)ethane
1-[Trans-4-(E-5-fluoro-4-pentenyl)cyclohexyl]-2-(3-fluoro-4-cyanophenyl)ethane
1-[Trans-4-(E-6-fluoro-5-hexenyl)cyclohexyl]-2-(3-fluoro-4-cyanophenyl)ethane
1-[Trans-4-(E-7-fluoro-6-heptenyl)cyclohexyl]-2-(3-fluoro-4-cyanophenyl)ethane
1-[Trans-4-(E-8-fluoro-7-octenyl)cyclohexyl]-2-(3-fluoro-4-cyanophenyl)ethane
Trans-1-[4-(E-2-fluoro-1-ethenyl)phenyl]-4-ethylcyclohexane
Trans-1-[4-(E-2-fluoro-1-ethenyl)phenyl]-4-propylcyclohexane
Trans-1-[4-(E-2-fluoro-1-ethenyl)phenyl]-4-butylcyclohexane
Trans-1-[4-(E-2-fluoro-1-ethenyl)phenyl]-4-pentylcyclohexane
Trans-1-[4-(E-2-fluoro-1-ethenyl)phenyl]-4-hexylcyclohexane
Trans-1-[4-(E-2-fluoro-1-ethenyl)phenyl]-4-methoxymethylcyclohexane
Trans-1-[4-(E-3-fluoro-2-propenyl)phenyl]-4-ethylcyclohexane
Trans-1-[4-(E-3-fluoro-2-propenyl)phenyl]-4-propylcyclohexane
Trans-1-[4-(E-3-fluoro-2-propenyl)phenyl]-4-butylcyclohexane
Trans-1-[4-(E-3-fluoro-2-propenyl)phenyl]-4-pentylcyclohexane
Trans-1-[4-(E-3-fluoro-2-propenyl)phenyl]-4-hexylcyclohexane
Trans-1-[4-(E-3-fluoro-2-propenyl)phenyl]-4-methoxymethylcyclohexane
Trans-1-[4-(E-4-fluoro-3-butenyl)phenyl]-4-ethylcyclohexane
Trans-1-[4-(E-4-fluoro-3-butenyl)phenyl]-4-propylcyclohexane
Trans-1-[4-(E-4-fluoro-3-butenyl)phenyl]-4-butylcyclohexane
Trans-1-[4-(E-4-fluoro-3-butenyl)phenyl]-4-pentylcyclohexane
Trans-1-[4-(E-4-fluoro-3-butenyl)phenyl]-4-hexylcyclohexane
Trans-1-[4-(E-4-fluoro-3-butenyl)phenyl]-4-methoxymethylcyclohexane
Trans-1-[3-fluoro-4-(E-2-fluoro-1-ethenyl)phenyl]-4-ethylcyclohexane
Trans-1-[3-fluoro-4-(E-2-fluoro-1-ethenyl)phenyl]-4-propylcyclohexane
Trans-1-[3-fluoro-4-(E-2-fluoro-1-ethenyl)phenyl]-4-butylcyclohexane
Trans-1-[3-fluoro-4-(E-2-fluoro-1-ethenyl)phenyl]-4-pentylcyclohexane
Trans-1-[3-fluoro-4-(E-2-fluoro-1-ethenyl)phenyl]-4-hexylcyclohexane
Trans-1-[3-fluoro-4-(E-2-fluoro-1-ethenyl)phenyl]-4-methoxymethylcyclohexane
Trans-1-[3-fluoro-4-(E-3-fluoro-2-propenyl)phenyl]-4-ethylcyclohexane
Trans-1-[3-fluoro-4-(E-3-fluoro-2-propenyl)phenyl]-4-propylcyclohexane Trans-1-[3-fluoro-4-(E-3-fluoro-2-propenyl)phenyl]-4-butylcyclohexane
Trans-1-[3-fluoro-4-(E-3-fluoro-2-propenyl)phenyl]-4-pentylcyclohexane
Trans-1-[3-fluoro-4-(E-3-fluoro-2-propenyl)phenyl]-4-hexylcyclohexane
Trans-1-[3-fluoro-4-(E-3-fluoro-2-propenyl)phenyl]-4-methoxymethylcyclohexane
Trans-1-[3-fluoro-4-(E-4-fluoro-3-butenyl)phenyl]-4-ethylcyclohexane
Trans-1-[3-fluoro-4-(E-4-fluoro-3-butenyl)phenyl]-4-propylcyclohexane
Trans-1-[3-fluoro-4-(E-4-fluoro-3-butenyl)phenyl]-4-butylcyclohexane
Trans-1-[3-fluoro-4-(E-4-fluoro-3-butenyl)phenyl]-4-pentylcyclohexane
Trans-1-[3-fluoro-4-(E-4-fluoro-3-butenyl)phenyl]-4-hexylcyclohexane
Trans-1-[3-fluoro-4-(E-4-fluoro-3-butenyl)phenyl]-4-methoxymethylcyclohexane
4-(E-2-fluoro-1-ethenyl)-4'-ethylbiphenyl
4-(E-2-fluoro-1-ethenyl)4'-propylbiphenyl
4-(E-2-fluoro-1-ethenyl)-4'-butylbiphenyl
4-(E-2-fluoro-1-ethenyl)-4'-pentylbiphenyl
4-(E-2-fluoro-1-ethenyl)-4'-hexylbiphenyl
4-(E-2-fluoro-1-ethenyl)-4'-methoxymethylbiphenyl
4-(E-2-fluoro-1-ethenyl)-4'-methoxybiphenyl
4-(E-2-fluoro-1-ethenyl)-4'-ethoxybiphenyl
4-(E-2-fluoro-1-ethenyl)-4'-propoxybiphenyl
4-(E-2-fluoro-1-ethenyl)-4'-butoxybiphenyl
4-(E-2-fluoro-1-ethenyl)-4'-pentyloxybiphenyl
4-(E-2-fluoro-1-ethenyl)-4'-hexyloxybiphenyl
4-(E-3-fluoro-2-propenyl)-4'-ethylbiphenyl
4-(E-3-fluoro-2-propenyl)-4'-propylbiphenyl
4-(E-3-fluoro-2-propenyl)-4'-butylbiphenyl
4-(E-3-fluoro-2-propenyl)-4'-pentylbiphenyl
4-(E-3-fluoro-2-propenyl)-4'-hexylbiphenyl
4-(E-3-fluoro-2-propenyl)-4'-methoxymethylbiphenyl
4-(E-3-fluoro-2-propenyl)-4'-methoxybiphenyl
4-(E-3-fluoro-2-propenyl)-4'-ethoxybiphenyl
4-(E-3-fluoro-2-propenyl)-4'-propoxybiphenyl
4-(E-3-fluoro-2-propenyl)-4'-butoxybiphenyl
4-(E-3-fluoro-2-propenyl)-4'-pentyloxybiphenyl
4-(E-3-fluoro-2-propenyl)-4'-hexyloxybiphenyl
4-(E-4-fluoro-3-butenyl)-4'-ethylbiphenyl
4-(E-4-fluoro-3-butenyl)-4'-propylbiphenyl
4-(E-4-fluoro-3-butenyl)-4'-butylbiphenyl
4-(E-4-fluoro-3-butenyl)-4'-pentylbiphenyl
4-(E-4-fluoro-3-butenyl)-4'-hexylbiphenyl
4-(E-4-fluoro-3-butenyl)-4'-methoxymethylbiphenyl
4-(E-4-fluoro-3-butenyl)-4'-methoxybiphenyl
4-(E-4-fluoro-3-butenyl)-4'-ethoxybiphenyl
4-(E-4-fluoro-3-butenyl)-4'-propoxybiphenyl
4-(E-4-fluoro-3-butenyl)-4'-butoxybiphenyl
4-(E-4-fluoro-3-butenyl)-4'-pentyloxybiphenyl
4-(E-4-fluoro-3-butenyl)-4'-hexyloxybiphenyl
Trans-1-(E-2-fluoro-1-ethenyl)-4-(trans-4-ethylcyclohexyl)cyclohexane
Trans-1-(E-2-fluoro-1-ethenyl)-4-(trans-4-propylcyclohexyl)cyclohexane
Trans-1-(E-2-fluoro-1-ethenyl)-4-(trans-4-butylcyclohexyl)cyclohexane
Trans-1-(E-2-fluoro-1-ethenyl)-4-(trans-4-pentylcyclohexyl)cyclohexane
Trans-1-(E-2-fluoro-1-ethenyl)-4-(trans-4-hexylcyclohexyl)cyclohexane
Trans-1-(E-2-fluoro-1-ethenyl)-4-(trans-4-methoxymethylcyclohexyl)cyclohexane
Trans-1-(E-3-fluoro-2-propenyl)-4-(trans-4-ethylcyclohexyl)cyclohexane
Trans-1-(E-3-fluoro-2-propenyl)-4-(trans-4-propylcyclohexyl)cyclohexane
Trans-1-(E-3-fluoro-2-propenyl)-4-(trans-4-butylcyclohexyl)cyclohexane
Trans-1-(E-3-fluoro-2-propenyl)-4-(trans-4-pentylcyclohexyl)cyclohexane
Trans-1-(E-3-fluoro-2-propenyl)-4-(trans-4-hexylcyclohexyl)cyclohexane
Trans-1-(E-3-fluoro-2-propyl)-4-(trans-4-methoxymethylcyclohexyl)cyclohexane
Trans-1-(E-4-fluoro-3-butenyl)-4-(trans-4-ethylcyclohexyl)cyclohexane
Trans-1-(E-4-fluoro-3-butenyl)-4-(trans-4-propylcyclohexyl)cyclohexane
Trans-1-(E-4-fluoro-3-butenyl)-4-(trans-4-butylcyclohexyl)cyclohexane
Trans-1-(E-4-fluoro-3-butenyl)-4-(trans-4-pentylcyclohexyl)cyclohexane.
Trans-1-(E-4-fluoro-3-butenyl)-4-(trans-4-hexylcyclohexyl)cyclohexane
Trans-1-(E-4-fluoro-3-butenyl)-4-(trans-4-methoxymethylcyclohexyl)cyclohexane
Trans-1-(E-2-fluoro-1-ethenyl)-4-(4-ethylphenyl)cyclohexane
Trans-1-(E-2-fluoro-1-ethenyl)-4-(4-propylphenyl)cyclohexane
Trans-1-(E-2-fluoro-1-ethenyl)-4-(4-butylphenyl)cyclohexane
Trans-1-(E-2-fluoro-1-ethenyl)-4-(4-pentylphenyl)cyclohexane
Trans-1-(E-2-fluoro-1-ethenyl)-4-(4-hexylphenyl)cyclohexane
Trans-1-(E-2-fluoro-1-ethenyl)-4-(4-methoxymethylphenyl)cyclohexane
Trans-1-(E-2-fluoro-1-ethenyl)-4-(4-ethoxyphenyl)cyclohexane
Trans-1-(E-2-fluoro-1-ethenyl)-4-(4-propoxyphenyl)cyclohexane
Trans-1-(E-2-fluoro-1-ethenyl)-4-(4-butoxyphenyl)cyclohexane
Trans-1-(E-2-fluoro-1-ethenyl)-4-(4-pentyloxyphenyl)cyclohexane
Trans-107 (E-2-fluoro-1-ethenyl)-4-(4-hexyloxyphenyl)cyclohexane
Trans-1-(E-3-fluoro-2-propenyl)-4-(4-ethylphenyl)cyclohexane
Trans-1-(E-3-fluoro-2-propenyl)-4-(4-propylphenyl)cyclohexane
Trans-1-(E-3-fluoro-2-propenyl)-4-(4-butylphenyl)cyclohexane
Trans-1-(E-3-fluoro-2-propenyl)-4-(4-pentylphenyl)cyclohexane
Trans-1-(E-3-fluoro-2-propenyl)-4-(4-hexylphenyl)cyclohexane
Trans-1-(E-3-fluoro-2-propenyl)-4-(4-methoxymethylphenyl)cyclohexane
Trans-1-(E-3-fluoro-2-propenyl)-4-(4-methoxyphenyl)cyclohexane
Trans-1-(E-3-fluoro-2-propenyl)-4-(4-ethoxyphenyl)cyclohexane
Trans-1-(E-3-fluoro-2-propenyl)-4-(4-propoxyphenyl)cyclohexane
Trans-1-(E-3-fluoro-2-propenyl)-4-(4-butoxyphenyl)cyclohexane
Trans-1-(E-3-fluoro-2-propenyl)-4-(4-pentyloxyphenyl)cyclohexane Trans-1-(E-3-fluoro-2-propenyl)-4-(4-hexyloxyphenyl)-cyclohexane
Trans-1-(E-4-fluoro-3-butenyl)-4-(4-ethylphenyl)cyclohexane
Trans-1-(E-4-fluoro-3-butenyl)-4-(4-propylphenyl)cyclohexane
Trans-1-(E-4-fluoro-3-butenyl)-4-(4-butylphenyl)cyclohexane
Trans-1-(E-4-fluoro-3-butenyl)-4-(4-pentylphenyl)cyclohexane
Trans-1-(E-4-fluoro-3-butenyl)-4-(4-hexylphenyl)cyclohexane
Trans-1-(E-4-fluoro-3-butenyl)-4-(4-methoxymethylphenyl)cyclohexane
Trans-1-(E-4-fluoro-3-butenyl)-4-(4-methoxyphenyl)-cyclohexane
Trans-1-(E-4-fluoro-3-butenyl)-4-(4-ethoxyphenyl)cyclohexane
Trans-1-(E-4-fluoro-3-butenyl)-4-(4-propoxyphenyl)cyclohexane
Trans-1-(E-4-fluoro-3-butenyl)-4-(4-butoxyphenyl)cyclohexane
Trans-1-(E-4-fluoro-3-butenyl)-4-(4-pentyloxyphenyl)-cyclohexane
Trans-1-(E-4-fluoro-3-butenyl)-4-(4-hexyloxyphenyl)-cyclohexane
1-[4-(E-2-fluoro-1-ethenyl)phenyl]-2-(trans-4-ethylcyclohexyl)ethane
1-[4-(E-2-fluoro-1-ethenyl)phenyl]-2-(trans-4-propylcyclohexyl)ethane
1-[4-(E-2-fluoro-1-ethenyl)phenyl]-2-(trans-4-butylcyclohexyl)ethane
1-[4-(E-2-fluoro-1-ethenyl)phenyl]-2-(trans-4-pentylcyclohexyl)ethane
1-[4-(E-2-fluoro-1-ethenyl)phenyl]-2-(trans-4-hexylcyclohexyl)ethane
1-[4-(E-2-fluoro-1-ethenyl)phenyl]-2-(trans-4-methoxymethylcyclohexyl)ethane
1-[4-(E-3-fluoro-2-propenyl)phenyl]-2-(trans-4-ethylcyclohexyl)ethane
1-[4-(E-3-fluoro-2-propenyl)phenyl]-2-(trans-4-propylcyclohexyl)ethane
1-[4-(E-3-fluoro-2-propenyl)phenyl]-2-(trans-4-butylcyclohexyl)ethane
1-[4-(E-3-fluoro-2-propenyl)phenyl]-2-(trans-4-pentylcyclohexyl)ethane
1-[4-(E-3-fluoro-2-propenyl)phenyl]-2-(trans-4-hexylcyclohexyl)ethane
1-[4-(E-3-fluoro-2-propenyl)phenyl]-2-(trans-4-methoxymethylcyclohexyl)ethane
1-[4-(E-4-fluoro-3-butenyl)phenyl]-2-(trans-4-ethylcyclohexyl)ethane
1-[4-(E-4-fluoro-3-butenyl)phenyl]-2-(trans-4-propylcyclohexyl)ethane
1-[4-(E-4-fluoro-3-butenyl)phenyl]-2-(trans-4-butylcyclohexyl)ethane
1-[4-(E-4-fluoro-3-butenyl)phenyl]-2-(trans-4-pentylcyclohexyl)ethane
1-[4-(E-4-fluoro-3-butenyl)phenyl]-2-(trans-4-hexylcyclohexyl)ethane
1-[4-(E-4-fluoro-3-butenyl)phenyl]-2-(trans-4-methoxymethylcyclohexyl)ethane.

Among the compound of the formula (I) of the present invention wherein n=1, examples of preferable compounds are those expressed by the following formulas:

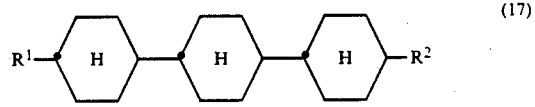
(17)

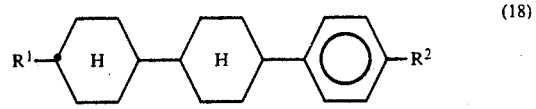
(18)

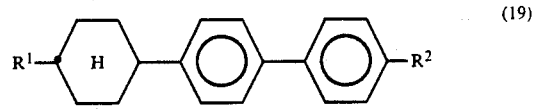
(19)

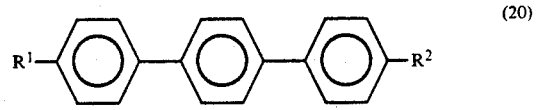
(20)

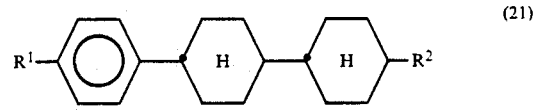
(21)

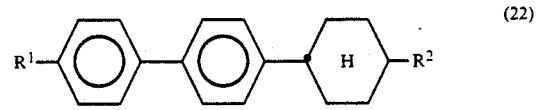
(22)

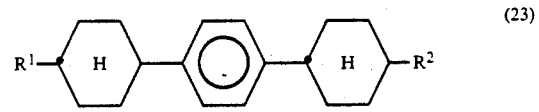
(23)

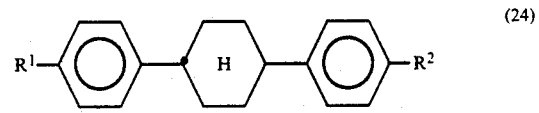
(24)

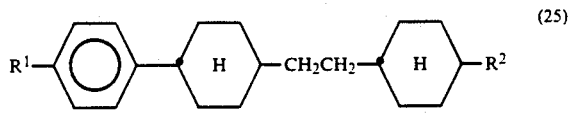
(25)

$R^1$ and $R^2$ in these formulas are as defined above, and the phenylene ring may be replaced by

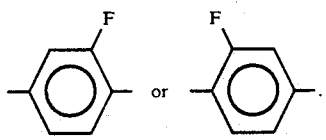

Among the compounds expressed by these formulas, those of the formulas wherein m in $R^2$ represents 0 to 6 are particularly preferred. Among compounds of the formulas (17) to (25), those of the formulas (20), (21), (22) and (25) are particularly preferred. Further, representative examples of particularly preferred compounds are as follows:

Trans-4-[trans-4-(E-2-fluoro-1-ethenyl)cyclohexyl]-1-(4-cyanophenyl)cyclohexane
Trans-4-[trans-4-(E-3-fluoro-2-propenyl)cyclohexyl]-1-(4-cyanophenyl)cyclohexane
Trans-4-[trans-4-(E-4-fluoro-3-butenyl)cyclohexyl]-1-(4-cyanophenyl)cyclohexane Trans-4-[trans-4-(E-5-fluoro-4-pentenyl)cyclohexyl]-1-(4-cyanophenyl)cyclohexane
Trans-4-[trans-4-(E-6-fluoro-5-hexenyl)cyclohexyl]-1-(4-cyanophenyl)cyclohexane
Trans-4-[trans-4-(E-7-fluoro-6-heptenyl)cyclohexyl]-1-(4-cyanophenyl)cyclohexane
Trans-4-[trans-4-(E-8-fluoro-7-octenyl)cyclohexyl]-1-(4-cyanophenyl)
Trans-4-[trans-4-(E-2-fluoro-1-ethenyl)cyclohexyl]-1-(4-fluorophenyl)cyclohexane
Trans-4-[trans-4-(E-3-fluoro-2-propenyl)cyclohexyl]-1-(4-fluorophenyl)cyclohexane
Trans-4-[trans-4-(E-4-fluoro-3-butenyl)cyclohexyl]-1-(4-fluorophenyl)cyclohexane
Trans-4-[trans-4-(E-5-fluoro-4-pentenyl)cyclohexyl]-1-(4-fluorophenyl)cyclohexane
Trans-4-[trans-4-(E-6-fluoro-5-hexenyl)cyclohexyl]-1-(4-fluorophenyl)cyclohexane
Trans-4-[trans-4-(E-7-fluoro-6-heptenyl)cyclohexyl]-1-(4-fluorophenyl)cyclohexane
Trans-4-[trans-4-(E-8-fluoro-7-octenyl)cyclohexyl]-1-(4-fluorophenyl)cyclohexane
Trans-4-[trans-4-(E-2-fluoro-1-ethenyl)cyclohexyl]-1-(3,4-difluorophenyl)cyclohexane
Trans-4-[trans-4-(E-3-fluoro-2-propenyl)cyclohexyl]-1-(3,4-difluorophenyl)cyclohexane
Trans-4-[trans-4-(E-4-fluoro-3-butenyl)cyclohexyl]-1-(3,4-difluorophenyl)cyclohexane
Trans-4-[trans-4-(E-5-fluoro-4-pentenyl)cyclohexyl]-1-(3,4-difluorophenyl)cyclohexane
Trans-4-[trans-4-(E-6-fluoro-5-hexenyl)cyclohexyl]-1-(3,4-difluorophenyl)cyclohexane
Trans-4-[trans-4-(E-7-fluoro-6-heptenyl)cyclohexyl]-1-(3,4-difluorophenyl)cyclohexane
Trans-4-[trans-4-(E-8-fluoro-7-octenyl)cyclohexyl]-1-(3,4-difluorophenyl)cyclohexane
Trans-4-[trans-4-(E-2-fluoro-1-ethenyl)cyclohexyl]-1-(3-fluoro-4-cyanophenyl)cyclohexane
Trans-4-[trans-4-(E-3-fluoro-2-propenyl)cyclohexyl]-1-(3-fluoro-4-cyanophenyl)cyclohexane
Trans-4-[trans-4-(E-4-fluoro-3-butenyl)cyclohexyl]-1-(3-fluoro-4-cyanophenyl)cyclohexane
Trans-4-[trans-4-(E-5-fluoro-4-pentenyl)cyclohexyl]-1-(3-fluoro-4-cyanophenyl)cyclohexane
Trans-4-[trans-4-(E-6-fluoro-5-hexenyl)cyclohexyl]-1-(3-fluoro-4-cyanophenyl)cyclohexane
Trans-4-[trans-4-(E-7-fluoro-6-heptenyl)cyclohexyl]-1-(3-fluoro-4-cyanophenyl)cyclohexane
Trans-4-[trans-4-(E-8-fluoro-7-octenyl)cyclohexyl]-1-(3-fluoro-4-cyanophenyl)cyclohexane
4-[Trans-4-(E-2-fluoro-1-ethenyl)cyclohexyl]-4'-cyanobiphenyl
4-[Trans-4-(E-3-fluoro-2-propenyl)cyclohexyl]-4'-cyanobiphenyl
4-[Trans-4-(E-4-fluoro-3-butenyl)cyclohexyl]-4'-cyanobiphenyl
4-[Trans-4-(E-5-fluoro-4-pentenyl)cyclohexyl]-4'-cyanobiphenyl
4-[Trans-4-(E-6-fluoro-5-hexenyl)cyclohexyl]-4'-cyanobiphenyl
4-[Trans-4-(E-7-fluoro-6-heptenyl)cyclohexyl]-4'-cyanobiphenyl
4-[Trans-4-(E-8-fluoro-7-octenyl)cyclohexyl]-4'-cyanobiphenyl
4-[Trans-4-(E-2-fluoro-1-ethenyl)cyclohexyl]-4'-fluorobiphenyl
4-[Trans-4-(E-3-fluoro-2-propenyl)cyclohexyl]-4'-fluorobiphenyl
4-[Trans-4-(E-4-fluoro-3-butenyl)cyclohexyl]-4'-fluorobiphenyl
4-[Trans-4-(E-5-fluoro-4-pentenyl)cyclohexyl]-4'-fluorobiphenyl
4-[Trans-4-(E-6-fluoro-5-hexenyl)cyclohexyl]-4'-fluorobiphenyl
4-[Trans-4-(E-7-fluoro-6-heptenyl)cyclohexyl]-4'-fluorobiphenyl
4-[Trans-4-(E-8-fluoro-7-octenyl)cyclohexyl]-4'-fluorobiphenyl
4-[Trans-4-(E-2-fluoro-1-ethenyl)cyclohexyl]-3',4'-difluorobiphenyl
4-[Trans-4-(E-3-fluoro-2-propenyl)cyclohexyl]-3',4'-difluorobiphenyl
4-[Trans-4-(E-4-fluoro-3-butenyl)cyclohexyl]-3',4'-difluorobiphenyl
4-[Trans-4-(E-5-fluoro-4-pentenyl)cyclohexyl]-3',4'-difluorobiphenyl
4-[Trans-4-(E-6-fluoro-5-hexenyl)cyclohexyl]-3',4'-difluorobiphenyl
4-[Trans-4-(E-7-fluoro-6-heptenyl)cyclohexyl]-3',4'-difluorobiphenyl
4-[Trans-4-(E-8-fluoro-7-octenyl)cyclohexyl]-3',4'-difluorobiphenyl
4-[Trans-4-(E-2-fluoro-1-ethenyl)cyclohexyl]-3'-fluoro-4'-cyanobiphenyl
4-[Trans-4-(E-3-fluoro-2-propenyl)cyclohexyl]-3'-fluoro-4'-cyanobiphenyl
4-[Trans-4-(E-4-fluoro-3-butenyl)cyclohexyl]-3'-fluoro-4'-cyanobiphenyl
4-[Trans-4-(E-5-fluoro-4-pentenyl)cyclohexyl]-3'-fluoro-4'-cyanobiphenyl
4 [Trans-4-(E-6-fluoro-5-hexenyl)cyclohexyl]-3'-fluoro-4'-cyanobiphenyl
4-[Trans-4-(E-7-fluoro-6-heptenyl)cyclohexyl]-3'-fluoro-4'-cyanobiphenyl
4-[Trans-4-(E-8-fluoro-7-octenyl)cyclohexyl]-3'-fluoro-4'-cyanobiphenyl
1-[Trans-4-(E-2-fluoro-1-ethenyl)cyclohexyl]-2-[trans-4-(4-cyanophenyl)cyclohexyl]ethane
1-[Trans-4-(E-3-fluoro-2-propenyl)cyclohexyl]-2-[trans-4-(4-cyanophenyl)cyclohexyl]ethane
1-[Trans-4-(E-4-fluoro-3-butenyl)cyclohexyl]-2-[trans-4-(4-cyanophenyl)cyclohexyl]ethane
1-[Trans-4-(E-5-fluoro-4-pentenyl)cyclohexyl]-2-[trans-4-(4-cyanophenyl)cyclohexyl]ethane
1-[Trans-4-(E-6-fluoro-5-hexenyl)cyclohexyl]-2-[trans-4-(4-cyanophenyl)cyclohexyl]ethane
1-[Trans-4-(E-7-fluoro-6-heptenyl)cyclohexyl]-2-[trans-4-(4-cyanophenyl)cyclohexyl]ethane
1-[Trans-4-(E-8-fluoro-7-octenyl)cyclohexyl]-2-[trans-4-(4-cyanophenyl)cyclohexyl]ethane
1-[Trans-4-(E-2-fluoro-1-ethenyl)cyclohexyl]-2-[trans-4-(4-fluorophenyl)cyclohexyl]ethane
1-[Trans-4-(E-3-fluoro-2-propenyl)cyclohexyl]-2-[trans-4-(4-fluorophenyl)cyclohexyl]ethane
1-[Trans-4-(E-4-fluoro-3-butenyl)cyclohexyl]-2-[trans-4-(4-fluorophenyl)cyclohexyl]ethane
1-[Trans-4-(E-5-fluoro-4-pentenyl)cyclohexyl]-2-[trans-4-(4-fluorophenyl)cyclohexyl]ethane
1-[Trans-4-(E-6-fluoro-5-hexenyl)cyclohexyl]-2-[trans-4-(4-fluorophenyl)cyclohexyl]ethane
1-[Trans-4-(E-7-fluoro-6-heptenyl)cyclohexyl]-2-[trans-4-(4-fluorophenyl)cyclohexyl]ethane
1-[Trans-4-(E-8-fluoro-7-octenyl)cyclohexyl]-2-[trans-4-(4-fluorophenyl)cyclohexyl]ethane
1-[Trans-4-(E-2-fluoro-1-ethenyl)cyclohexyl]-2-[trans-4-(3-fluoro-4-cyanophenyl) cyclohexyl]ethane 1-[Trans-4-(E-3-fluoro-2-propenyl)cyclohexyl]-2-
[trans-4-(3-fluoro-4-cyanophenyl) cyclohexyl]ethane
1-[Trans-4-(E-4-fluoro-3-butenyl)cyclohexyl]-2-]trans-
4-(3-fluoro-4-cyanophenyl) cyclohexyl]ethane
1-[Trans-4-(E-5-fluoro-4pentenyl)cyclohexyl]-2-[trans-
4-(3-fluoro-4-cyanophenyl) cyclohexyl]ethane
1-[Trans-4-(E-6-fluoro-5-hexenyl)cyclohexyl]-2-[trans-
4-(3-fluoro-4-cyanophenyl) cyclohexyl]ethane
1-[Trans-4-(E-7-fluoro-6-heptenyl)cyclohexyl]-2-
[trans-4-(3-fluoro-4-cyanophenyl) cyclohexyl]ethane
1-[Trans-4-(E-8-fluoro-7-octenyl)cyclohexyl]-2-[trans-
4-(3-fluoro-4-cyanophenyl) cyclohexyl]ethane
1-[Trans-4-(E-2-fluoro-1-ethenyl)cyclohexyl]-2-[trans-
4-(3,4-difluorophenyl)cyclohexyl]ethane
1-[Trans-4-(E-3-fluoro-2-propenyl)cyclohexyl]-2-
[trans-4-(3,4-difluorophenyl)cyclohexyl]ethane
1-[Trans-4-(E-4-fluoro-3-butenyl)cyclohexyl]-2-[trans-
4-(3,4-difluorophenyl)cyclohexyl]ethane
1-[Trans-4-(E-5-fluoro-4-pentenyl)cyclohexyl]-2-[trans-
4-(3,4-difluorophenyl)cyclohexyl]ethane
1-[Trans-4-(E-6-fluoro-5-hexenyl)cyclohexyl]-2-[trans-
4-(3,4-difluorophenyl)cyclohexyl]ethane
1-[Trans-4-(E-7-fluoro-6-heptenyl)cyclohexyl]-2-[trans-
4-(3,4-difluorophenyl)cyclohexyl]ethane
1-[Trans-4-(E-8-fluoro-7-octenyl)cyclohexyl]-2-[trans-
4-(3,4-difluorophenyl)cyclohexyl]ethane
Trans-4-[trans-4-(E-2-fluoro-1-ethenyl)cyclohexyl]-1-
(4- ethylphenyl)cyclohexane
Trans-4-[trans-4-(E-2-fluoro-1-ethenyl)cyclohexyl]-1-
(4-propylphenyl)cyclohexane
Trans-4-[trans-4-(E-2-fluoro-1-ethenyl)cyclohexyl]-1-
(4-butylphenyl)cyclohexane
Trans-4-[trans-4-(E-2-fluoro-1-ethenyl)cyclohexyl]-1-
(4-pentylphenyl)cyclohexane
Trans-4-[trans-4-(E-2-fluoro-1-ethenyl)cyclohexyl]-1-
(4-hexylphenyl)cyclohexane
Trans-4-[trans-4-(E-2-fluoro-1-ethenyl)cyclohexyl]-20
1-(4-methoxymethylphenyl)cyclohexane
Trans-4-[trans-4-(E-2-fluoro-1-ethenyl)cyclohexyl]-1-
(4-methoxyphenyl)cyclohexane
Trans-4-[trans-4-(E-2-fluoro-1-ethenyl)cyclohexyl]-1-
(4-ethoxyphenyl)cyclohexane
Trans-4-[trans-4-(E-2-fluoro-1-ethenyl)cyclohexyl]-1-
(4-propoxyphenyl)cyclohexane
Trans-4-[trans-4-(E-2-fluoro-1-ethenyl)cyclohexyl]-1-
(4-butoxyphenyl)cyclohexane
Trans-4-[trans-4-(E-2-fluoro-1-ethenyl)cyclohexyl]-1-
(4-pentyloxyphenyl)cyclohexane
Trans-4-[trans-4-(E-2-fluoro-1-ethenyl)cyclohexyl]-1-
(4-hexyloxyphenyl)cyclohexane
Trans-4-[trans-4-(E-3-fluoro-2-propenyl)cyclohexyl]-1-
(4-ethylphenyl)cyclohexane
Trans-4-[trans-4-(E-3-fluoro-2-propenyl)cyclohexyl]-1-
(4-propylphenyl)cyclohexane
Trans-4-[trans-4-(E-3-fluoro-2-propenyl)cyclohexyl]-1-
(4-butylphenyl)cyclohexane
Trans-4-[trans-4-(E-3-fluoro-2-propenyl)cyclohexyl]-1-
(4-pentylphenyl)cyclohexane
Trans-4-[trans-4-(E-3-fluoro-2-propenyl)cyclohexyl]-1-
(4-hexylphenyl)cyclohexane
Trans-4-[trans-4-(E-3-fluoro-2-propenyl)cyclohexyl]-1-
(4-methoxymethylphenyl)cyclohexane
Trans-4-[trans-4-(E-3-fluoro-2-propenyl)cyclohexyl]-1-
(4-methoxyphenyl)cyclohexane
Trans-4-[trans-4-(E-3-fluoro-2-propenyl)cyclohexyl]-1-
(4-ethoxyphenyl)cyclohexane
Trans-4-[trans-4-(E-3-fluoro-2-propenyl)cyclohexyl]-1-
(4-propoxyphenyl)cyclohexane
Trans-4-[trans-4-(E-3-fluoro-2-propenyl)cyclohexyl]-1-
(4-butoxyphenyl)cyclohexane
Trans-4-[trans-(E-3-fluoro-2-propenyl)cyclohexyl]-1-
(4-pentyloxyphenyl)cyclohexane
Trans-4-[trans-4-(E-3-fluoro-2-propenyl)cyclohexyl]-1-
(4-hexyloxyphenyl)cyclohexane
Trans-4-[trans-4-(E-4-fluoro-3-butenyl)cyclohexyl]-1-
(4-ethylphenyl)cyclohexane
Trans-4-[trans-4-(E-4-fluoro-3-butenyl)cyclohexyl]-1-
(4-propylphenyl)cyclohexane
Trans-4-[trans-4-(E-4-fluoro-3-butenyl)cyclohexyl]-1-
(4-butylphenyl)cyclohexane
Trans-4-[trans-4-(E-4-fluoro-3-butenyl)cyclohexyl]-1-
(4-pentylphenyl)cyclohexane
Trans-4-[trans-4-(E-4-fluoro-3-butenyl)cyclohexyl]-1-
(4-hexylphenyl)cyclohexane
Trans-4-[trans-4-(E-4-fluoro-3-butenyl)cyclohexyl]-1-
(4-methoxymethylphenyl)cyclohexane
Trans-4-[trans-4-(E-4-fluoro-3-butenyl)cyclohexyl]-1-
(4-methoxyphenyl)cyclohexane
Trans-4-[trans-4-(E-4-fluoro-3-butenyl)cyclohexyl]-1-
(4-ethoxyphenyl)cyclohexane
Trans-4-[trans-4-(E-4-fluoro-3-butenyl)cyclohexyl]-1-
(4-propoxyphenyl)cyclohexane
Trans-4-[trans-4-(E-4-fluoro-3-butenyl)cyclohexyl]-1-
(4-butoxyphenyl)cyclohexane
Trans-4-[trans-4-(E-4-fluoro-3-butenyl)cyclohexyl]-1-
(4-pentyloxyphenyl)cyclohexane
Trans-4-[trans-4-(E-4-fluoro-3-butenyl)cyclohexyl]-1-
(4-hexyloxyphenyl)cyclohexane
4-[Trans-4-(E-2-fluoro-1-ethenyl)cyclohexyl]-4'-ethyl-
biphenyl
4-[Trans-4-(E-2-fluoro-1-ethenyl)cyclohexyl]-4'-
propylbiphenyl
4-[Trans-4-(E-2-fluoro-1-ethenyl)cyclohexyl]-4'-butyl-
biphenyl
4-[Trans-4-(E-2-fluoro-1-ethenyl)cyclohexyl]-4'-pentyl-
biphenyl
4-[Trans-4-(E-2-fluoro-1-ethenyl)cyclohexyl]-4'-hexyl-
biphenyl
4-[Trans-4-(E-2-fluoro-1-ethenyl)cyclohexyl]-4'-
methoxymethylbiphenyl
4-[Trans-4-(E-2-fluoro-1-ethenyl)cyclohexyl]-4'-
methoxybiphenyl
4-[Trans-4-(E-2-fluoro-1-ethenyl)cyclohexyl]-4'-ethox-
ybiphenyl
4-[Trans-4-(E-2-fluoro-1-ethenyl)cyclohexyl]-4'-
propoxybiphenyl
4-[Trans-4-(E-2-fluoro-1-ethenyl)cyclohexyl]-4'-butox-
ybiphenyl
4-[Trans-4-(E-2-fluoro-1-ethenyl)cyclohexyl]-4'-pen-
tyloxybiphenyl
4-[Trans-4-(E-2-fluoro-1-ethenyl)cyclohexyl]-4'-hex-
yloxybiphenyl
4-[Trans-4-(E-3-fluoro-2-propenyl)cyclohexyl]-4'-
ethylbiphenyl
4-[Trans-4-(E-3-fluoro-2-propenyl)cyclohexyl]-4'-
propylbiphenyl
4-[Trans-4-(E-3-fluoro-2-propenyl)cyclohexyl]-4'-
butylbiphenyl
-[Trans-4-(E-3-fluoro-2-propenyl)cyclohexyl]-4'-pen-
tylbiphenyl
4-[Trans-4-(E-3-fluoro-2-propenyl)cyclohexyl]-4'-hex-
ylbiphenyl
4-[Trans-4-(E-3-fluoro-2-propenyl)cyclohexyl]-4'-
methoxymethylbiphenyl
4-[Trans-4-(E-3-fluoro-2-propenyl)cyclohexyl]-4'-
methoxybiphenyl 4-[Trans-4-(E-3-fluoro-2-propenyl)cyclohexyl]-4'-ethoxybiphenyl
4-[Trans-4-(E-3-fluoro-2-propenyl)cyclohexyl]-4'-propoxybiphenyl
4-[Trans-4-(E-3-fluoro-2-propenyl)cyclohexyl]-4'-butoxybiphenyl
4-[Trans-4-(E-3-fluoro-2-propenyl)cyclohexyl]-4'-pentyloxybiphenyl
4-[Trans-4-(E-3-fluoro-2-propenyl)cyclohexyl]-4'-hexyloxybiphenyl
4-[Trans-4-(E-4-fluoro-3-butenyl)cyclohexyl]-4'-ethylbiphenyl
4-[Trans-4-(E-4-fluoro-3-butenyl)cyclohexyl]-4'-propylbiphenyl
4-[Trans-4-(E-4-fluoro-3-butenyl)cyclohexyl]-4'-butylbiphenyl
4-[Trans-4-(E-4-fluoro-3-butenyl)cyclohexyl]-4'-pentylbiphenyl
4-[Trans-4-(E-4-fluoro-3-butenyl)cyclohexyl]-4'-hexylbiphenyl
4-[Trans-4-(E-4-fluoro-3-butenyl)cyclohexyl]-4'-methoxymethylbiphenyl
4-[Trans-4-(E-4-fluoro-3-butenyl)cyclohexyl]-4'-methoxybiphenyl
4-[Trans-4-(E-4-fluoro-3-butenyl)cyclohexyl]-4'-ethoxybiphenyl
4-[Trans-4-(E-4-fluoro-3-butenyl)cyclohexyl]-4'-propoxybiphenyl
4-[Trans-4-(E-4-fluoro-3-butenyl)cyclohexyl]-4'-butoxybiphenyl
4-[Trans-4-(E-4-fluoro-3-butenyl)cyclohexyl]-4'-pentyloxybiphenyl
4-[Trans-4-(E-4-fluoro-3-butenyl)cyclohexyl]-4'-hexyloxybiphenyl
1-[Trans-4-(E-2-fluoro-1-ethenyl)cyclohexyl]-2-[trans-4-(4-ethylphenyl)cyclohexyl]ethane
1-[Trans-4-(E-2-fluoro-1-ethenyl)cyclohexyl]-2-[trans-4-(4-propylphenyl)cyclohexyl]ethane
1-[Trans-4-(E-2-fluoro-1-ethenyl)cyclohexyl]-2-[trans-4-(4-butylphenyl)cyclohexyl]ethane
1-[Trans-4-(E-2-fluoro-1-ethenyl)cyclohexyl]-2-[trans-4-(4-pentylphenyl)cyclohexyl]ethane
1-[Trans-4-(E-2-fluoro-1-ethenyl)cyclohexyl]-2-[trans-4-(4-hexylphenyl)cyclohexyl]ethane
1-[Trans-4-(E-2-fluoro-1-ethenyl)cyclohexyl]-2-[trans-4-(4-methoxymethylphenyl)cyclohexyl]ethane
1-[Trans-4-(E-2-fluoro-1-ethenyl)cyclohexyl]-2-[trans-4-(4-methoxyphenyl)cyclohexyl]ethane
1-[Trans-4-(E-2-fluoro-1-ethenyl)cyclohexyl]-2-[trans-4-(4-ethoxyphenyl)cyclohexyl]ethane
1-[Trans-4-(E-2-fluoro-1-ethenyl)cyclohexyl]-2-[trans-4-(4-propoxyphenyl)cyclohexyl]ethane
1-[Trans-4-(E-2-fluoro-1-ethenyl)cyclohexyl]-2-[trans-4-(4-butoxyphenyl)cyclohexyl]ethane
1-[Trans-4-(E-2-fluoro-1-ethenyl)cyclohexyl]-2-[trans-4-(4-pentyloxyphenyl)cyclohexyl]ethane
1-[Trans-4-(E-2-fluoro-1-ethenyl)cyclohexyl]-2-[trans-4-(4-hexyloxyphenyl)cyclohexyl]ethane
1-[Trans-4-(E-3-fluoro-2-propenyl)cyclohexyl]-2-[trans-4-(4-ethylphenyl)cyclohexyl]ethane
1-[Trans-4-(E-3-fluoro-2-propenyl)cyclohexyl]-2-[trans-4-(4-propylphenyl)cyclohexyl]ethane
1-[Trans-4-(E-3-fluoro-2-propenyl)cyclohexyl]-2-[trans-4-(4-butylphenyl)cyclohexyl]ethane
1-[Trans-4-(E-3-fluoro-2-propenyl)cyclohexyl]-2-[trans-4-(4-pentylphenyl)cyclohexyl]ethane
1-[Trans-4-(E-3-fluoro-2-propenyl)cyclohexyl]-2-[trans-4-(4-hexylphenyl)cyclohexyl]ethane
1-[Trans-4-(E-3-fluoro-2-propenyl)cyclohexyl]-2-[trans-4-(4-methoxymethylphenyl)cyclohexyl]ethane
1-[Trans-4-(E-3-fluoro-2-propenyl)cyclohexyl]-2-[trans-4-(4-methoxyphenyl)cyclohexyl]ethane
1-[Trans-4-(E-3-fluoro-2-propenyl)cyclohexyl]-2-[trans-4-(4-ethoxyphenyl)cyclohexyl]ethane
1-[Trans-4-(E-3-fluoro-2-propenyl)cyclohexyl]-2-[trans-4-(4-propoxyphenyl)cyclohexyl]ethane
1-[Trans-4-(E-3-fluoro-2-propenyl)cyclohexyl]-2-[trans-4-(4-butoxyphenyl)cyclohexyl]ethane
1-[Trans-4-(E-3-fluoro-2-propenyl)cyclohexyl]-2-[trans-4-(4-pentyloxyphenyl)cyclohexyl]ethane
1-[Trans-4-(E-3-fluoro-2-propenyl)cyclohexyl]-2-[trans-4-(4-hexyloxyphenyl)cyclohexyl]ethane
1-[Trans-4-(E-4-fluoro-3-butenyl)cyclohexyl]-2-[trans-4-(4-ethylphenyl)cyclohexyl]ethane
1-[Trans-4-(E-4-fluoro-3-butenyl)cyclohexyl]-2-[trans-4-(4-propylphenyl)cyclohexyl]ethane
1-[Trans-4-(E-4-fluoro-3-butenyl)cyclohexyl]-2-[trans-4-(4-butylphenyl)cyclohexyl]ethane
1-[Trans-4-(E-4-fluoro-3-butenyl)cyclohexyl]-2-[trans-4-(4-pentylphenyl)cyclohexyl]ethane
1-[Trans-4-(E-4-fluoro-3-butenyl)cyclohexyl]-2-[trans-4-(4-hexylphenyl)cyclohexyl]ethane
1-[Trans-4-(E-4-fluoro-3-butenyl)cyclohexyl]-2-[trans-4-(4-methoxymethylphenyl)cyclohexyl]ethane
1-[Trans-4-(E-4-fluoro-3-butenyl)cyclohexyl]-2-[trans-4-(4-methoxyphenyl)cyclohexyl]ethane
1-[Trans-4-(E-4-fluoro-3-butenyl)cyclohexyl]-2-[trans-4-(4-ethoxyphenyl)cyclohexyl]ethane
1-[Trans-4-(E-4-fluoro-3-butenyl)cyclohexyl]-2-[trans-4-(4-propoxyphenyl)cyclohexyl]ethane
1-[Trans-4-(E-4-fluoro-3-butenyl)cyclohexyl]-2-[trans-4-(4-butoxyphenyl)cyclohexyl]ethane
1-[Trans-4-(E-4-fluoro-3-butenyl)cyclohexyl]-2-[trans-4-(4-pentyloxyphenyl)cyclohexyl]ethane
1-[Trans-4-(E-4-fluoro-3-butenyl)cyclohexyl]-2-[trans-4-(4-hexyloxyphenyl)cyclohexyl]ethane The compound of the present invention may be prepared for example according to the following synthesis:

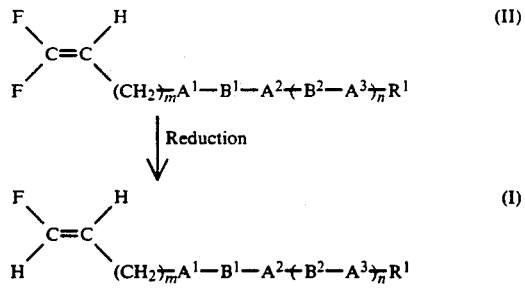

The compound of the present invention is obtained by reducing a 2,2-difluoroethene derivative expressed by the formula (II) with a metal hydride such as lithium aluminum hydride, lithium tri(tert-butoxy)aluminum hydride, sodium bis(2-methoxyethoxy)aluminum hydride, etc., preferably sodium bis(2-methoxyethoxy)aluminum hydride. Herein, in the case of a compound of the formula (I) wherein $R^1$ represents a cyano group, the compound may be prepared for example according to the following synthesis:

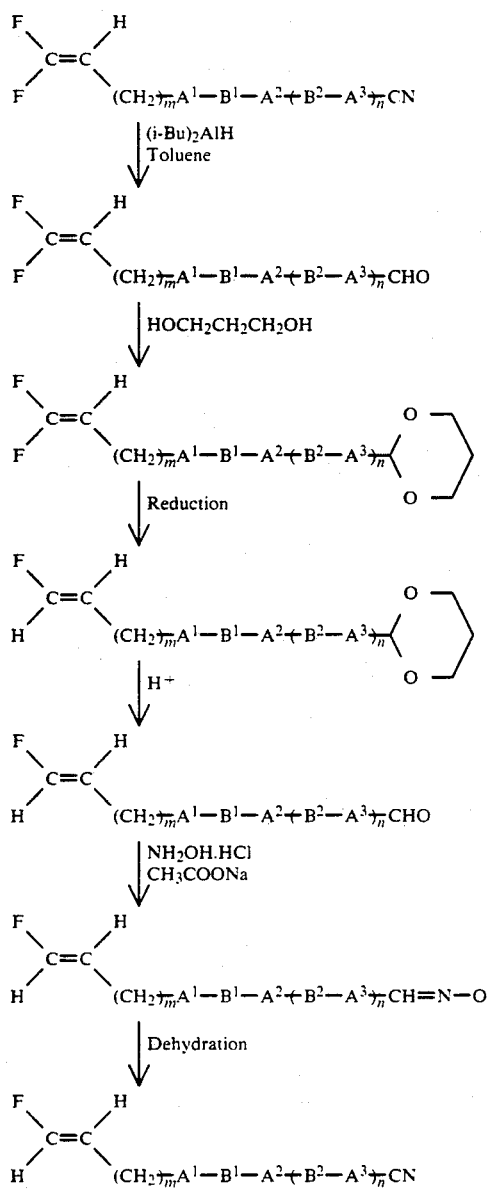

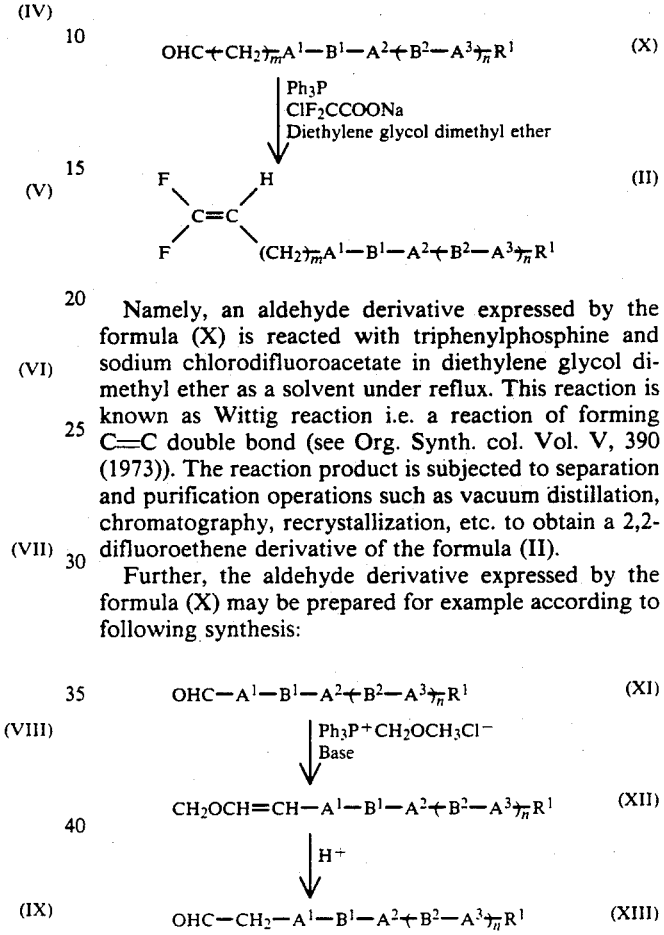

Namely, a substituted benzonitrile or a substituted cyclohexanecarbonitrile expressed by the formula (III) is reacted with diisobutylaluminum hydride at a low temperature in dry toluene solvent to obtain the corresponding aldehyde derivative (IV), followed by subjecting the aldehyde derivative expressed by the formula (IV) and triethylene glycol to dehydration-condensation reaction to obtain a dioxane derivative expressed by the formula (V), reducing the compound expressed by the formula (V), with a metal hydride such as sodium bis(2-methoxyethoxy)aluminum hydride to obtain a compound expressed by the formula (VI), hydrolyzing the compound of the formula (VI) under an acidic condition to obtain an aldehyde derivative expressed by the formula (VII), subjecting the aldehyde derivative of the formula (VII) and hydroxylamine to condensation reaction to obtain an oxime derivative expressed by the formula (VIII), and reacting the compound of the formula (VIII) with a dehydrating agent such as acetic anhydride, acetic anhydride-sodium acetate, thionyl chloride, phosphorus pentoxide, phosphorus pentachloride, benzoyl chloride or the like to obtain a nitrile derivative of the formula (IX). This nitrile derivative (IX) is a compound of the formula (I) wherein $R^1$ represent cyano group.

The 2,2-difluoroethene derivative expressed by the formula (II), as the starting raw material, may be prepared for example according to the following synthesis:

Namely, an aldehyde derivative expressed by the formula (X) is reacted with triphenylphosphine and sodium chlorodifluoroacetate in diethylene glycol dimethyl ether as a solvent under reflux. This reaction is known as Wittig reaction i.e. a reaction of forming C=C double bond (see Org. Synth. col. Vol. V, 390 (1973)). The reaction product is subjected to separation and purification operations such as vacuum distillation, chromatography, recrystallization, etc. to obtain a 2,2-difluoroethene derivative of the formula (II).

Further, the aldehyde derivative expressed by the formula (X) may be prepared for example according to following synthesis:

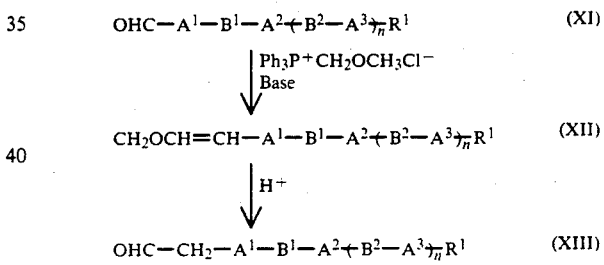

Namely, according to Wittig reaction of reacting an aldehyde derivative (XI) with methoxymethyltriphenylphosphonium chloride and a base such as potassium t-butoxide, sodium methoxide, phenyllithium, n-butyllithium, etc., a methoxyvinyl derivative (XII) is obtained. When this compound (XII) is heated under an acidic condition, for example, heated with hydrochloric acid in tetrahydrofuran solvent, an aldehyde derivative (XIII) having one methylene group added to the original aldehyde derivative (XI) can be obtained. By m times repeating the Wittig reaction and the acid treatment reaction using the aldehyde derivative (XI) as the raw material, an aldehyde derivative (X) having methylene group(s) in the number of m of 1 or more can be obtained.

Most of the aldehyde derivative expressed by the formula (XI) are known compounds or homologues of known compounds, and the rest of the derivatives, too, may easily be prepared by combining known reactions with known compounds. Further, the aldehyde derivative expressed by the formula (XI) may also be obtained by reducing or oxidizing the corresponding nitrile derivative, benzoic acid derivative, cyclohexanecarboxylic acid derivative, benzyl alcohol derivative, cyclohexyl methanol, etc.

The compound of the formula (I) of the present invention is a compound having a relatively low viscosity and suitable for preparing a liquid crystal display device having a higher response rate.

The compound of the present invention has stabilities to heat, light, electricity, air, moisture, etc. required for liquid crystal materials. Further, since the compound of the present invention has a superior compatibility with other liquid crystalline compounds, it is possible to prepare liquid crystal materials suitable to various use applications, by mixing the compound with these compounds or mixtures thereof.

A liquid crystal composition of the present invention may preferably contain as other components than compounds expressed by the formula (I), liquid crystal compounds expressed by the following formulas (i)–(xxxiii):

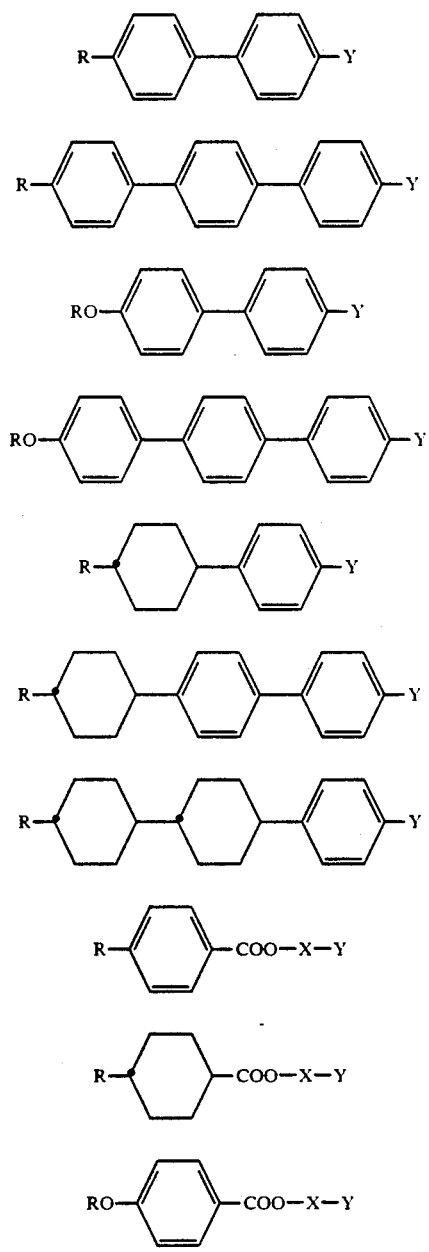

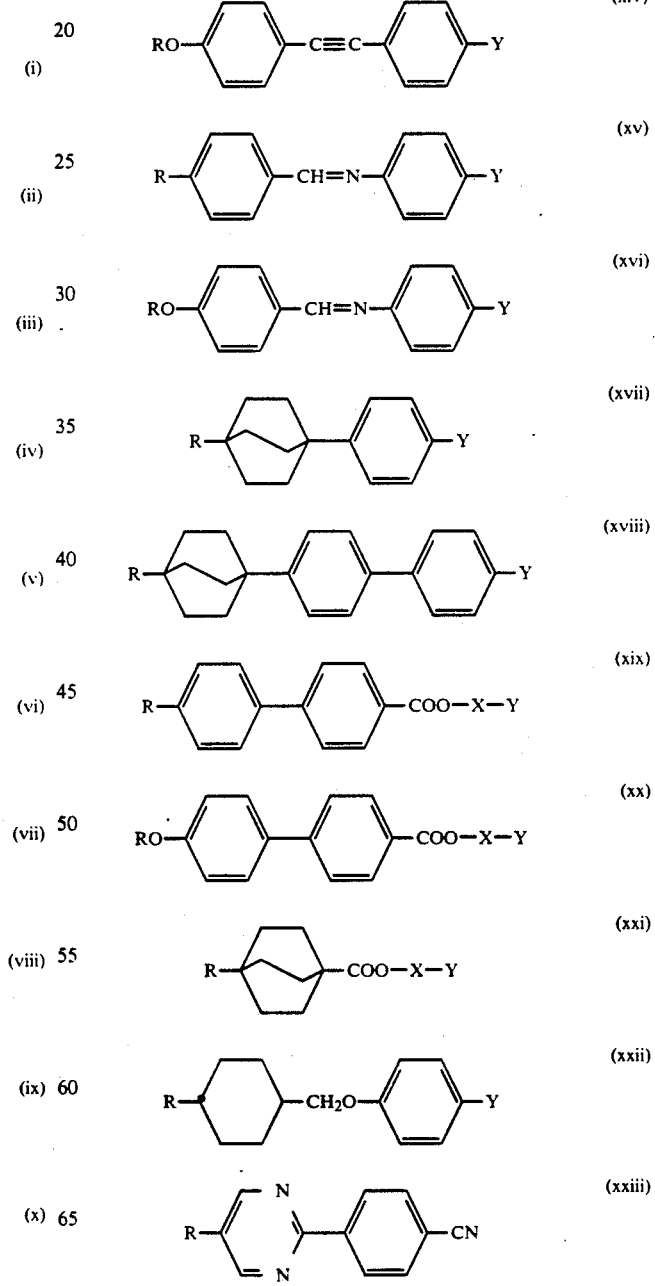

21

-continued

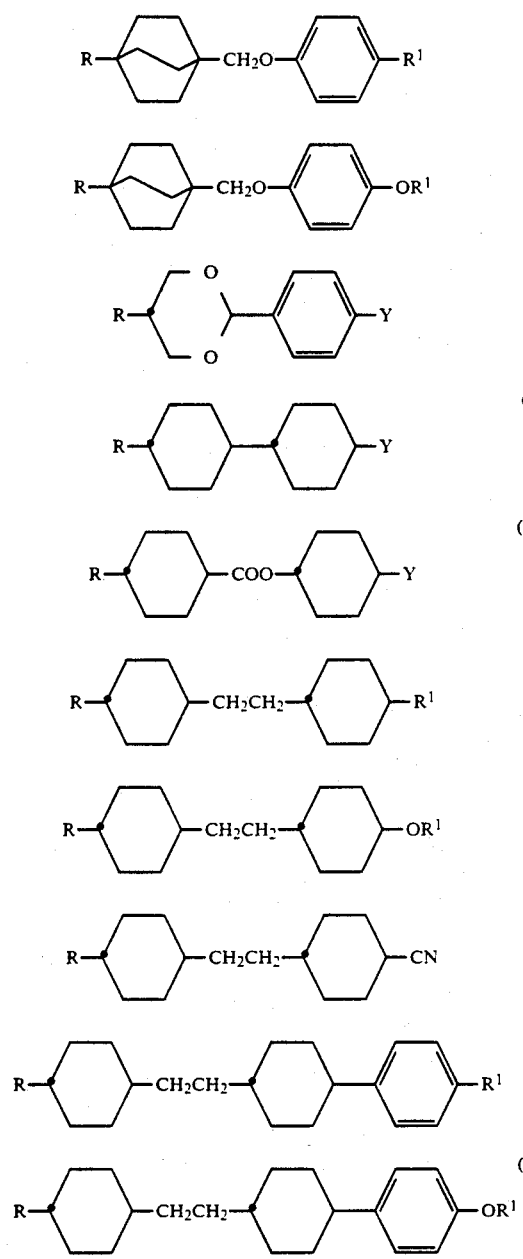

In these formula (i)-(xxxiii), X represents

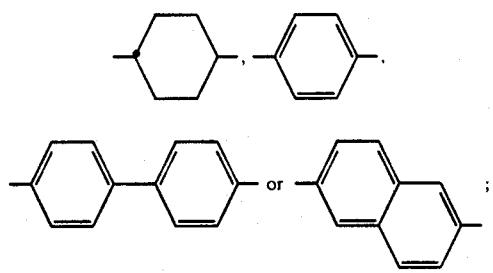

Y represents —CN, halogen atoms, $R^1$ or $OR^1$; R and $R^1$ each represent an alkyl group; and the hydrogen atom(s) of

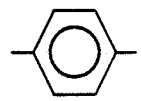

may be replaced by halogen atom(s).

By using the compound of the present invention, when several kinds of liquid crystalline compounds are mixed to prepare liquid crystal materials suitable to various display devices, it is possible to make a good choice of the liquid crystalline component compounds.

The compound of the present invention forms a liquid crystal phase within a temperature range suitable to liquid crystal display devices. Further, the compound of the present invention includes a number of compounds having nematic phase within a broad temperature range, and when these compounds are added to nematic crystal compositions, they have characteristics of raising the nematic-isotropic liquid crystal phase transition point thereof or not lowering it so much.

The compound of the present invention is a colorless compound in its pure state. Further, among the compound of the present invention, those having cyano group have a large positive dielectric anisotropy value and also a relatively large optical anisotropy value; thus they are suitable to display elements utilizing an electro-optical effect.

The two-ring compounds of the above formulas (1)–(16) have a low viscosity and a superior compatibility with other existing liquid crystals, and those of the formulas (1)–(8) are particularly preferred. Further, many of the three-ring compounds of the above formulas (17)–(25) have a higher clearing point than those of the two-ring compounds.

The present invention will be described in more detail by way of Examples, but it should not be construed to be limited thereto.

In Examples, crystalline-smectic phase transition point, crystalline-nematic phase transition point, smectic-nematic phase transition point, nematic-isotropic liquid phase transition point and crystalline-isotropic liquid crystal phase transition point are abbreviated to CS point, CN point, SN point, NI point, SI point and CI point, respectively.

EXAMPLE 1

Preparation of trans-1-(E-2-fluoro-1-ethenyl)-4-(4-cyanophenyl)cyclohexane (i) Preparation of trans-4-(4-cyanophenyl)cyclohexanecarbaldehyde Trimethylsilyl chloride (305.6 g, 2.81 mol) was dropwise added to trans-4-methoxymethyl-1-(4-cyanophenyl)cyclohexane (322.5 g, 1.41 mol), sodium iodide (421.6 g, 2.81 mol) and acetonitrile (2.5 l), with stirring in nitrogen atmosphere at 35° C. over 30 minutes, followed by agitating the mixture for 20 minutes, cooling it down to 10° C., filtering the reaction mixture by suction, pouring the mother liquor in ice water (2 Kg), extracting with chloroform (1.5 l), twice washing the chloroform solution with a 10% by weight aqueous solution of sodium thiosulfate (0.5 l), further three times washing with water (1 l), distilling off chloroform, and three times recrystallizing the residue from toluene (300 ml) for purification to obtain trans-4-(4-cyanophenyl)-cyclohexylcarbinol (182.5 g, 0.848 mol). M.P.:

108.5–110.8° C. A solution of this trans-4-(4-cyanophenyl)cyclohexylcarbinol (107.6 g, 0.500 mol) in dichloromethane (0.7 l) was instantaneously added to a solution of pyridinium chlorochromate (161.7 g, 0.750 mol) in dichloromethane (1 l), prepared in advance, with stirring, at room temperature, followed by agitating the mixture at room temperature for 1.5 hour, adding diethyl ether (1 l) to the resulting reaction solution, and subjecting the supernatant to column chromatography using Florisil ® (made by Floridin Co., Ltd.) as a filler to obtain trans-4-(4-cyanophenyl)cyclohexylcarbaldehyde (101.2 g, 0.474 mol).

(ii) Preparation of trans-1-(2,2-difluoro-1-ethenyl)-4-(4-cyanophenyl)cyclohexane Trans-4-(4-cyanophenyl)cyclohexylcarbaldehyde (47.8 g, 0.224 mol) obtained above in (i), triphenylphosphine (64.6 g, 0.246 mol), sodium chlorodifluoroacetate (54.6 g, 0.538 mol) and dimethylformamide (200 ml) were heated to about 90° C. for 3 hours with stirring in nitrogen current followed by cooling the resulting solution down to room temperature, adding toluene (200 ml) and water (200 ml) to the solution, three times washing the resulting toluene solution with water (200 ml), drying over anhydrous sodium sulfate, separating the drying agent, distilling off toluene, subjecting the residue to vacuum distillation (b.p. 136°–138° C./1 mmHg), dissolving the distillate in toluene, purifying according to silica gel chromatography, repeating recrystallization from methanol, and drying to obtain trans-1-(2,2-difluoro-1-ethenyl)-4-(4-cyanophenyl)cyclohexane (20.3 g, 0.0821 mol). This compound had a m.p. of 59.3° C. and an NI point of 9.8° C. (monotropic).

(iii) Preparation of trans-1-(2,2-difluoro-1-ethenyl)-4-(4-formylphenyl)cyclohexane A reaction system of trans-1-(2,2-difluoro-1-ethenyl)-4-(4-cyanophenyl)cyclohexane obtained above in (ii) (57.0 g, 0.23 mol) and toluene (400 ml) was purged with nitrogen with stirring at 0° C., followed by gradually adding a 25 wt. % toluene solution (170 ml) of diisobutylaluminum hydride, with stirring at a reaction temperature of 5° C. or lower in nitrogen current, further agitating the mixture at a reaction temperature of 5° C. for one hour, dropwise adding methanol (50 ml), water (50 ml) and further 6N-hydrochloric acid (300 ml) with stirring while keeping the reaction temperature at 20° C. or lower, removing the aqueous layer of the reaction mixture, five times washing the residue with a saturated aqueous solution of sodium hydrogen carbonate (200 ml), further washing with water till the aqueous layer became neutral, drying the toluene solution over anhydrous sodium sulfate, filtering off the drying agent and drying the resulting residue under reduced pressure to obtain the objective substance (56 g, 0.22 mol).

(iv) Preparation of trans-1-(2,2-difluoro-1-ethenyl)-4-{4-(1,3-dioxan-2-yl)phenyl}cyclohexane Trans-1-(2,2-difluoro-1-ethenyl)-4-(4-formylphenyl)cyclohexane (56 g, 0.22 mol) obtained above in (iii), triethylene glycol (25 g, 0.33 mol), p-toluenesulfonic acid hydrate (0.4 g, 0.002 mol) and toluene (200 m() were reacted in a flask fixed with a Dean-Stark trap and a condenser under reflux on heating for 10 hours, followed by cooling the reaction mixture, washing with a 5% aqueous solution of sodium hydrogen carbonate and further with water, drying the resulting toluene layer over anhydrous magnesium sulfate, distilling off toluene to obtain a residue (69 g), repeatedly recrystallizing it from ethanol and drying to obtain the objective substance (45 g, 0.15 mol). M.P.: 71–73° C.

(v) Preparation of trans-1-(E-2-fluoro-1-ethenyl)-4-{4-(1,3-dioxan-2-yl)phenyl}cyclohexane Trans-1-(2,2-difluoro-1-ethenyl)-4-{4-(1,3-dioxan-2-yl)phenyl}cyclohexane (38 g, 0.12 mol) obtained above in (iv), a 74% by weight toluene solution (80 ml) of sodium bis(2-methoxyethoxy)aluminum hydride and toluene (90 ml) were heated under reflux with stirring in nitrogen current for 10 hours, followed by cooling the reaction mixture, gradually pouring the solution in ice (200 g), adding toluene (100 ml), washing the resulting toluene solution with 6N-hydrochloric acid and further with water, drying the toluene solution over anhydrous magnesium sulfate and distilling off toluene to obtain the objective substance (34 g, 0.12 mol; E:Z=5:1).

(vi) Preparation of trans-1-(E-2-fluoro-1-ethenyl)-4-(4-formylphenyl)cyclohexane Trans-1-(E-2-fluoro-1-ethenyl)-4-{4-(1,3-dioxan-2-yl)phenyl}cyclohexane (34 g, 0.12 mol), tetrahydrofurane (130 ml) and 3N-hydrochloric acid (130 ml) were heated under reflux with stirring for 5 hours, followed by cooling the reaction mixture, adding toluene (200 ml) and water (200 ml) to the mixture, washing the resulting toluene solution with water, drying over anhydrous magnesium sulfate and distilling off toluene to obtain the objective substance (25 g, 0.11 mol; E:Z=5:1).

(vii) Preparation of 4-{trans-4-(E-2-fluoro-1-ethenyl)-cyclohexyl}benzaldehyde oxime Trans-1-(E-2-fluoro-1-ethenyl)-4-(4-formylphenyl)-cyclohexane (25 g, 0.11 mol) obtained above in (vi), ethanol (80 ml), hydroxylamine hydrochloride (9.7 g, 0.14 mol), sodium acetate (26 g, 0.19 mol) and water (50 ml) were heated under reflux with stirring for 3 hours, followed by cooling the reaction mixture, pouring it in water (500 ml), filtering the mixture through a funnel by suction, washing the residue on the filter with heptane (100 ml) and drying it under reduced pressure to obtain the objective substance (25.6 g, 0.10 mol; E:Z=5:1).

(viii) Preparation of trans-1-(E-2-fluoro-1-ethenyl)-4-(4-cyanophenyl)cyclohexane 4-{Trans-4-(E-2-fluoro-1-ethenyl)cyclohexyl}-benzaldehyde oxime (25.6 g, 0.10 mol) obtained above in (vii) and acetic anhydride (130 ml) were heated under reflux with stirring for 3 hours, followed by cooling the reaction solution, pouring it in water (300 ml), extracting with toluene (200 ml), washing the resulting toluene solution with water and further with a saturated aqueous solution of sodium hydrogen carbonate and still further with water till the aqueous layer became neutral, drying the toluene solution over anhydrous magnesium sulfate, distilling off toluene to obtain a residue (24 g), dissolving it in toluene/heptane (1:1 ratio by volume), purifying the solution according to silica gel chromatography, repeatedly recrystallizing from heptane/ethanol (4:1 ratio by volume) and drying to obtain the objective trans-1-(E-2-fluoro-1-ethenyl)-4-(4-cyanophenyl)cyclohexane (8.0 g, 0.035 mol). This compound exhibited a CI point of 82° C. and an NI point of 70° C. (monotropic).

EXAMPLE 2

Preparation of trans-1-(E-4-fluoro-3-butenyl)-4-(4-cyanophenyl)cyclohexane (i) Preparation of trans-4-(4-cyanophenyl)cyclohexylacetaldehyde Commercially available methoxymethyltriphenylphosphonium chloride (127.5 g, 0.372 mol) was added to methyl t-butyl ether (1 ℓ), followed by adding potassium t-butoxide (43.1 g, 0.384 mol) in argon atmosphere with stirring at −10° C. over 10 minutes, agitating the reaction mixture at 0° C. for one hour, dropwise adding a solution of trans-4-(4-cyanophenyl)cyclohexylcarbaldehyde (44.1 g, 0.207 mol) obtained above in Example 1 (i) in methyl t-butyl ether (200 ml) at −10° C over 15 minutes, agitating the reaction mixture at 0° C. for one hour, adding toluene (0.3 l) and water (0.3 l), four times washing the resulting toluene solution with water (0.3 l), drying over anhydrous sodium sulfate, separating the drying agent, distilling off toluene, dissolving the residue in ethyl acetate (100 ml) on heating, allowing the solution to stand at room temperature for one day, filtering off the deposited crystals, concentrating the mother liquor, dissolving the concentrate in heptane, purifying the solution according to silica gel chromatography to obtain trans-1-(2-methoxy-1-ethenyl)-4-(4-cyanophenyl)cyclohexane (39.8 g, 0.165 mol), adding to the total quantity, tetrahydrofuran (500 mℓ) and 2N-hydrochloric acid (120 mℓ), heating the mixture under reflux with stirring for one hour, cooling the reaction mixture, washing by adding toluene (300 ml) and water (1 l), further three times washing the resulting toluene solution with water (1 l), drying over anhydrous sodium sulfate, separating the drying agent, and distilling off toluene to obtain trans-(4-cyanophenyl)cyclohexylacetaldehyde (35.4 g. 0.156 mol).

(ii) Preparation of 3-[trans-4-(4-cyanophenyl)cyclohexyl]-1-propanal

Commercially available methoxymethyltriphenylphosphonium chloride (15.7 g, 0.0458 mol) was added to tetrahydrofuran (100 ml), followed by dropwise adding a 25% by weight toluene solution (23 ml) of phenyllithium in argon atmosphere with stirring at −10° C. over 10 minutes, agitating the reaction mixture at 0° C. for 30 minutes, dropwise adding a tetrahydrofuran solution (90 ml) of trans-4-(4-cyanophenyl)cyclohexylacetaldehyde (7.3 g, 0.032 mol) obtained in Example 2 (i) at −10° C. over 10 minutes, agitating the reaction mixture at 0° C. for 2 hours, washing by adding toluene (100 ml) and water (200 ml), further three times washing the toluene solution with water (200 ml), drying over anhydrous sodium sulfate, separating the drying agent, distilling off toluene, dissolving the residue in ethyl acetate (20 ml) on heating, allowing the solution to stand at room temperature for one day, filtering off deposited crystals, concentrating the mother liquor, dissolving the concentrate in heptane, purifying by silica gel column chromatography to obtain trans-1-(3-methoxy-2-propenyl-4-(4-cyanophenyl)cyclohexane (4.4 g, 0.017 mol), adding to the total quantity, tetrahydrofuran (70 ml) and 2N-hydrochloric acid (18 ml), heating the mixture for 1h. under reflux with stirring, cooling the reaction mixture, adding diethyl ether (50 ml) and water (50 ml), three times washing the resulting diethyl ether solution with water (50 ml), drying it over anhydrous sodium sulfate, separating the drying agent, and distilling off diethyl ether to obtain 3-[trans-4-(4-cyanophenyl)cyclohexyl]-1-propanal (4.2 g, 0.017 mol).

(iii) Preparation of trans-1-(4,4-difluoro-3-butenyl)-4-(4-cyanophenyl)cyclohexane 3-[Trans-4-(4-cyanophenyl)cyclohexyl]-1-propanal (4.2 g, 0.017 mol) obtained above in (ii), triphenylphosphine (5.2 g, 0.020 mol), sodium chlorodifluoroacetate (4.5 g, 0.029 mol) and dimethylformamide (30 ml) were heated in nitrogen current with stirring at ca. 90° C., for 3 hours, followed by cooling the reaction mixture and water (100 ml) to the reaction mixture, three times washing the resulting diethyl ether solution with water (100 ml), drying over anhydrous sodium sulfate, separating the drying agent, distilling off diethyl ether, dissolving the residue in hexane, purifying it according to silica gel column chromatography and repeating recrystallization from ethanol to obtain trans-1-(4,4-difluoro-3-butenyl)-4-(4-cyanophenyl)cyclohexane (1.6 g, 0.0058 mol). This compound had a CN point of 12° C. and an NI point of 28° C.

(iv) Preparation of trans-1-(E-4-fluoro-3-butenyl)-4-(4-cyanophenyl)cyclohexane

Using trans-1-(4,4-difluoro-3-butenyl)-4-(4-cyanophenyl)cyclohexane obtained above in (iii), as a raw material, trans-1-(E-4-fluoro-3-butenyl)-4-(4-cyanophenyl)cyclohexane was prepared similarly to the procedure in Example 1 (iii)-(viii). This compound had a CI point of 74° C. and an NI point of 68° C. (monotropic).

EXAMPLE 3

Preparation of trans-1-[4-(E-2-fluoro-1-ethenyl)phenyl]-4-propylcyclohexane (i) Preparation of 4-(trans-propylcyclohexyl)benzaldehyde Trans-4-propyl-(4-cyanophenyl)cyclohexane (100 g, 0.44 mol) and dry toluene (200 ml) were purged with nitrogen gas at 0° C. with stirring, followed by gradually adding a 25% by weight toluene solution (300 g) of diisobutylaluminum hydride in nitrogen current with stirring at a reaction temperature of 5° C. or lower, gradually raising the reaction temperature up to 20° C. over 3 hours, agitating the reaction mixture in nitrogen current at 20° C. for 10 hours, cooling it down to 0° C., dropwise adding methanol (200 ml), water (200 ml) and further 6N-hydrochloric acid (500 ml) with stirring, adding toluene (300 ml) to the reaction mixture to extract the resulting product, five times washing the resulting toluene solution with a saturated aqueous solution of sodium hydrogen carbonate (200 ml) and further with water till the aqueous layer became neutral, drying the toluene solution over anhydrous sodium sulfate, filtering off the drying agent, distilling off toluene and distilling the residue in vacuo (160° C., 2 mmHg) to obtain the objective substance (89 g, 0.39 mol). (ii) Preparation of trans-4-propyl-[4-(2,2-difluoro-1-ethenyl)phenyl]cyclohexane 4-(Trans-4-n-propylcyclohexyl)benzaldehyde (25 g, 0.11 mol), triphenylphosphine (31 g, 0.12 mol) and diethylene glycol dimethyl ether (25 ml) were heated with stirring in nitrogen current at 160° C., during which a solution of sodium chlorodifluoroacetate (25 g, 0.16 mol) in diethylene glycol dimethyl ether (70 ml) at 70° C. was added to the above solution over 2 hours, followed by cooling the resulting solution, filtering by suction, concentrating the filtrate under reduced pressure, distilling the concentrate in vacuo (150° C., 3 mmHg), dissolving the distillate in toluene (100 ml), three times washing the toluene solution with 6N-hydrochloric acid (100 ml), further washing with water till the aqueous layer became neutral, drying the toluene solution over anhydrous sodium sulfate, separating the drying agent, distilling off toluene, recrystallizing the resulting residue from a mixed solvent of heptane and ethanol (1:5), dissolving the resulting crystals in heptane, purifying according to silica gel column chromatography, again vacuum-distilling, three times recrystallizing from a mixed solvent of heptane and ethanol (1:5) and drying &o obtain the objective substance (10 g, 0.04 mol). This compound exhibited a CN point of 7° C. and an NI point of 48° C.

(iii) Preparation of trans-1-[4-(E-2-fluoro-1-ethenyl)-phenyl]-4-propylcyclohexane To trans-4-propyl-[4-(2,2-difluoro-1-ethenyl)phenyl]-cyclohexane (23.4 g, 0.089 mol) were gradually added benzene (50 ml) and a 70 wt. % toluene solution of sodium bis(2-methoxyethoxy)aluminum hydride (50 ml) at a reaction temperature of −5° C. or lower with stirring, followed by gradually raising the reaction temperature up to 0° C. over 20 minutes, pouring the reaction solution in ice water (500 ml), extracting the resulting product with toluene (300 ml), twice washing with 6N-HCl (300 ml), further washing with water till the aqueous layer became neutral, drying the toluene solution over anhydrous magnesium sulfate, filtering off the drying agent, distilling off toluene, dissolving the residue in heptane, purifying according to silica gel chromatography, vacuum-distilling (130° C., 1.2 mmHg), five times recrystallizing from a mixed solvent of heptane and ethanol (1:1) and drying to obtain the objective substance (2.66 g, 0.011 mol). This compound exhibited a CN point of 24° C. and an NI point of 70° C.

EXAMPLE 4

Preparation of trans-1-(E-2-fluoro-1-ethenyl)-4-(trans-4-propylcyclohexyl)cyclohexane (i) Preparation of trans-1-(2,2-difluoro-1-ethenyl)-4-(trans-4-propylcyclohexyl)cyclohexane Using trans-4-(trans-4-propylcyclohexyl)cyclohexanecarbonitrile as a starting raw material and similarly to the procedure as in Example 3, (i) and (ii), trans-1-(2,2-difluoro-1-ethenyl)-4-(trans-4-propylcyclohexyl)cyclohexane was prepared.

(ii) Preparation of trans-1-(E-2-fluoro-1-ethenyl)-4-(trans-4-propylcyclohexyl)cyclohexane To trans-1-(2,2-difluoro-1-ethenyl)-4-(trans-4-propylcyclohexyl)cyclohexane (44.0 g, 0.16 mol) were added toluene (250 ml) and a 70 wt. % toluene solution of sodium bis(2-methoxyethoxy)aluminum hydride (120 ml), followed by reacting the mixture under reflux on heating with stirring for 15 hours, cooling the reaction mixture, pouring it in ice water (300 ml), extracting the resulting product with toluene (300 ml), three times washing with 6N-hydrochloric acid (300 ml), washing with water till the aqueous layer became neutral, drying the toluene solution over anhydrous magnesium sulfate, filtering off the drying agent, distilling off toluene, dissolving the residue in heptane, purifying according to silica gel chromatography, repeating crystallization from hexane solvent and drying to obtain the objective substance (2.1 g, 0.008 mol). This compound exhibited a CS point of −13° C., an SN point of 43° C. and an NI point of 80° C.

EXAMPLE 5

Preparation of 4-pentyl-4'-(E-2-fluoro-1-ethenyl)biphenyl

Using 4-pentyl-4'-cyanobiphenyl as a starting raw material and similarly to the procedure in Example 3, (i), (ii) and (iii), 4-pentyl-4'-(E-2-fluoro-1-ethenyl)biphenyl was prepared. This compound exhibited an SI point of 123° C.

EXAMPLE 6

(Use Example 1)

A liquid crystal composition A consisting of

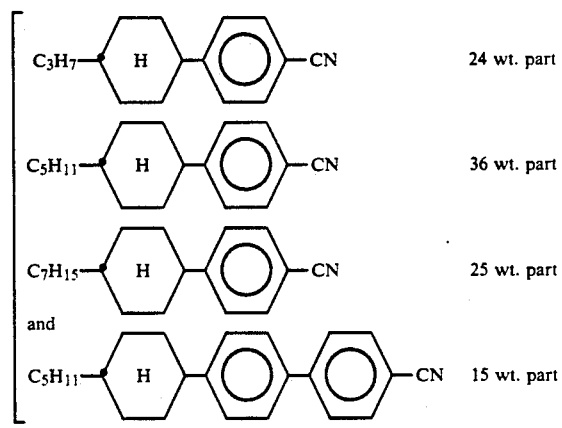

has an NI point of 72.0° C., a viscosity at 20° C. ($\eta_{20}$) of 27.5 cp, a $\Delta\epsilon$ of 11.0 ($\epsilon_{//}$15.7 and $\epsilon_{195}$=4.7) and a $\Delta n$ of 0.137 ($n_e$=1.632 and $n_o$=1.495). When the composition A was sealed in a TN cell having a cell thickness of 9 μm, it exhibited a threshold voltage of 1.78 V.

When 15 parts by weight of trans-1-(E-2-fluoro-1-ethenyl)-4-(4-cyanophenyl)cyclohexane shown in Example 1 was added to 85 parts by weight of the liquid crystal composition A, the resulting liquid crystal composition B exhibited an NI point of 71.2° C., that is, not lowered so much, a $\eta_{20}$ of 24.4 cp, that is, far lowered, a $\Delta\epsilon$ of 10.8 ($\epsilon_{//}$=15.3 and $\epsilon_{195}$=4.5) and a $\Delta n$ of 0.140 ($n_e$=1.636 and $n_o$=1.495). When the composition B was sealed in the above TN cell, the resulting cell exhibited a threshold voltage of 1.84 V.

EXAMPLE 7

(Use Example 2)

When 10 parts by weight of trans-1-(E-4-fluoro-3-butenyl)-4-(4-cyanophenyl)cyclohexane shown in Example 2 as a compound of the present invention was added to 90 parts by weight of the liquid crystal composition A used in Example 6, the resulting liquid crystal composition C exhibited an NI point of 70.1° C., that is, not lowered so much, a $\eta_{20}$ of 28.0 cp, a $\Delta\epsilon$ of 10.7 ($\epsilon_{//}$=15.8 and $\epsilon_{\perp}$=5.1) and a $\Delta n$ of 0.137 ($n_e$=1.629 and $n_o$1.492).

EXAMPLE 8

(Use Example 3)

When 15 parts by weight of trans-1-[4-(E-2-fluoro-1-ethenyl)phenyl]-4-propylcyclohexane shown in Example 3 as a compound of the present invention was added to 85 parts by weight of the liquid crystal composition A used in Example 6, the resulting liquid crystal composition D exhibited an NI point of 70.3° C., that is, not lowered so much, a $\eta_{20}$ of 20.5 cp, that is, far reduced, a $\Delta\epsilon$ of 10.1 ($\epsilon_{//}=14.4$ and $\epsilon_{\perp}=4.3$) and a $\Delta n$ of 0.131 ($n_e=1.630$ and $n_o=1.494$). When the composition D was sealed in the above TN cell, the resulting cell exhibited a threshold voltage of 1.87 V.

EXAMPLE 9

(Use Example 4)

When 15 parts by weight of trans-1-(E-2-fluoro-1-ethenyl)-4-(trans-4-propylcyclohexyl)cyclohexane shown in Example 4 as a compound of the present invention was added to 85 parts by weight of the liquid crystal composition A used in Example 6, the resulting liquid crystal composition E exhibited an NI point of 73.3° C., that is, elevated, a $\eta_{20}$ of 21.4 cp, that is, far lowered, a $\Delta\epsilon$ of 9.75 ($\epsilon_{//}=14.00$ and $\Delta_{\perp}=4.25$) and a $\Delta n$ of 0.128 ($n_e=1.618$ and $n_o=1.490$). When this composition E was sealed in the above TN cell, the resulting cell exhibited a threshold voltage of 1.91 V.

EXAMPLE 10

(Use Example 5)

When 15 parts by weight of 4-pentyl-4'-(E-2-fluoro-1-ethenyl)biphenyl shown in Example 5 as a compound of the present invention was added to 85 parts by weight of the liquid crystal composition A used in Example 6, the resulting liquid crystal composition F exhibited an NI point of 71.5° C., that is, not lowered so much, a $\eta_{20}$ of 21.1 cp. that is, far lowered, a $\Delta\epsilon$ of 10.2 ($\epsilon_{//}=14.6$ and $\epsilon_{\perp}=4.4$) and a $\Delta n$ of 0.144 ($n_e=1.642$ and $n_o=1.498$). When this composition F was kept in the above described cell, the liquid crystal cell exhibited a threshold voltage of 1.84 V.

As described above, the present invention provides a novel compound used as a component of materials for liquid crystal display.

When this compound is added to a liquid crystal mixture as its component, it affords &he above-mentioned effectiveness upon characteristics of liquid crystal materials.

What we claim:

1. A compound expressed by the formula

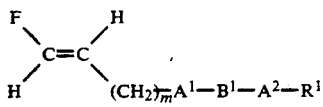

(I)

wherein $R^1$ represents a hydrogen atom, a fluorine atom, a chlorine atom, a cyano group, or an alkyl group or an alkenyl group each of 1 to 20 carbon atoms in which one —CH$_2$— group or two non-adjacent —CH$_2$— groups may be replaced by —O—, and in which alkenyl group the position and number of double bonds may be optionally chosen; $A^1$ and $A^2$ each independently represents

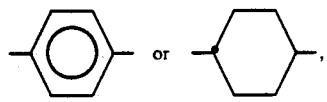

the hydrogen atoms(s) of which

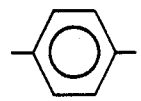

may be replaced by fluorine atom(s), chlorine atom(s) or methyl group(s); $B^1$ represents —CH$_2$CH$_2$—, —CH$_2$O—, —OCH$_2$— or a single bond; and m represents an integer of 0 to 20.

2. A compound according to claim 1 wherein in the formula (I) $R^1$ represents a fluorine atom, a chlorine atom, a cyano group, or an alkyl group of 1-20 carbon atoms; and m represents an integer of 0 to 6.

3. A compound according to claim 1 wherein in the formula (I) $R^1$ represents a fluorine atom, a chlorine atom, a cyano group, or an alkyl group of 1-20 carbon atoms; m represents an integer of 0 to 6; and $B^1$ represents —CH$_2$CH$_2$— or a single bond.

4. A compound according to claim 3 wherein in the formula (I) $B^1$ represents a single bond.

5. A compound according to claim 1, expressed by the formula

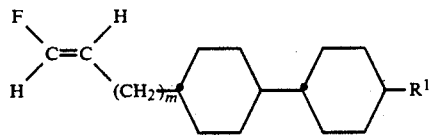

wherein $R^1$ is an alkyl group of 2 to 6 carbon atoms; and m is an integer of 0 to 6.

6. A compound according to claim 1, expressed by the formula

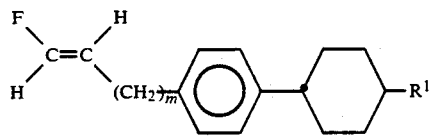

wherein $R^1$ is an alkyl group of 2 to 6 carbon atoms; and m is an integer of 0 to 6.

7. A compound according to claim 1, expressed by the formula

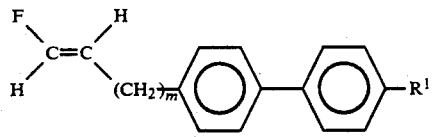

wherein $R^1$ is an alkyl group of 2 to 6 carbon atoms; and m is an integer of 0 to 6.

8. A compound according to claim 1, expressed by the formula

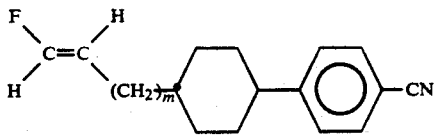

wherein m is an integer of 0 to 6.

9. A liquid crystal composition comprising at least two components at least one of which is a compound as set forth in claim 1.

* * * * *